(12) United States Patent
Prattichizzo et al.

(10) Patent No.: US 11,871,900 B2
(45) Date of Patent: Jan. 16, 2024

(54) INSTRUMENT COMPRISING A CONTACT FORCE SENSOR DEVICE

(71) Applicant: UNIVERSITÀ DEGLI STUDI DI SIENA, Siena (IT)

(72) Inventors: Domenico Prattichizzo, Siena (IT); Chiara Gaudeni, Lapedona (IT); Leonardo Meli, Siena (IT)

(73) Assignee: UNIVERSITÀ DEGLI STUDI DI SIENA, Siena (IT)

( * ) Notice: Subject to any disclaimer, the term of this patent is extended or adjusted under 35 U.S.C. 154(b) by 607 days.

(21) Appl. No.: 17/251,167

(22) PCT Filed: Jun. 11, 2019

(86) PCT No.: PCT/IB2019/054882
§ 371 (c)(1),
(2) Date: Dec. 10, 2020

(87) PCT Pub. No.: WO2019/239331
PCT Pub. Date: Dec. 19, 2019

(65) Prior Publication Data
US 2021/0251714 A1 Aug. 19, 2021

(30) Foreign Application Priority Data

Jun. 11, 2018 (IT) .................. 102018000006185

(51) Int. Cl.
*A61B 90/00* (2016.01)
*A61B 34/30* (2016.01)
*A61B 34/00* (2016.01)
*A61B 1/00* (2006.01)
(Continued)

(52) U.S. Cl.
CPC .......... *A61B 90/06* (2016.02); *A61B 1/00082* (2013.01); *A61B 17/00234* (2013.01);
(Continued)

(58) Field of Classification Search
CPC ................ A61B 90/06; A61B 1/00082; A61B 17/00234; A61B 34/30; A61B 34/76;
(Continued)

(56) References Cited

U.S. PATENT DOCUMENTS 5,487,730 A * 1/1996 Marcadis .............. A61M 25/10
604/103.07
5,807,326 A * 9/1998 O'Neill ............. A61M 25/1002
606/194

(Continued)

FOREIGN PATENT DOCUMENTS

CN 111166490 A * 5/2020 ............. A61B 34/30
JP 4472849 B2 * 6/2010 ......... A61B 1/00082
(Continued)

*Primary Examiner* — Francis C Gray
(74) *Attorney, Agent, or Firm* — Maschoff Brennan

(57) ABSTRACT

A contact force sensor device (10) comprises a gas-inflatable balloon (20) 5 arranged to switch from a deflated state (D) to an inflated state (J) in which it protrudes out of a support member (11); a valve assembly (34) to inflate/deflate the gas-inflatable balloon (12) with a gas; a detector (41) of a force-related value related to a force acting on the inflated gas-inflatable balloon (20) including a membrane (22) due to a contact with a wall (90) 10 outside of support member (11); a processing unit (60) configured to receive a detection signal (45) and to consequently calculate a contact force signal (54) according to a predetermined function; and a notification device (70) configured to receive the contact force signal (54) and to notify it to a user. The value detected can be an excess pressure ΔP in gas-15 inflatable balloon 20, or a deformation parameter of gas-inflatable balloon 20 caused by the contact, or a strain or stress modification in membrane 22, all these effect being caused by the contact with wall 90. Due to its simple structure and small size, the contact force sensor device (10), can be advantageously used in an diagnostic or surgical instrument since, 20 deflated, it (Continued)

can be easily inserted into a patient's body through a very small entry site, possibly along with a surgical or diagnostic tool to perform a mini-invasive surgical or diagnostic operation.

20 Claims, 11 Drawing Sheets

(51) Int. Cl.
    *A61B 17/00*     (2006.01)
    *B25J 13/08*     (2006.01)
    *G01L 1/02*     (2006.01)
    *B25J 15/00*     (2006.01)

(52) U.S. Cl.
    CPC .............. *A61B 34/30* (2016.02); *A61B 34/76* (2016.02); *A61B 90/39* (2016.02); *B25J 13/085* (2013.01); *B25J 15/0009* (2013.01); *G01L 1/02* (2013.01); *A61B 2034/305* (2016.02); *A61B 2090/065* (2016.02)

(58) Field of Classification Search
    CPC .............. A61B 2090/065; B25J 13/085; B25J 15/0009; G01L 1/02
    See application file for complete search history.

(56) References Cited

U.S. PATENT DOCUMENTS

| | | | | |
|---|---|---|---|---|
| 6,942,680 | B2 * | 9/2005 | Grayzel | A61F 2/958 623/1.11 |
| 7,606,615 | B2 * | 10/2009 | Makower | A61M 25/0069 600/407 |
| 7,678,075 | B2 * | 3/2010 | Wantink | A61M 25/10 604/96.01 |
| 7,887,661 | B2 * | 2/2011 | Chiu | A61M 25/10 156/308.2 |
| 2003/0229286 | A1 * | 12/2003 | Lenker | A61B 8/445 600/462 |
| 2010/0022918 | A1 | 1/2010 | Fujie | |
| 2012/0255985 | A1 | 10/2012 | Ma | |
| 2013/0190688 | A1 | 7/2013 | Knorr | |
| 2013/0197493 | A1 | 8/2013 | Strohmayr | |
| 2017/0333125 | A1 | 11/2017 | Lepak et al. | |
| 2017/0340236 | A1 | 11/2017 | Ghaffari | |

FOREIGN PATENT DOCUMENTS

| | | | |
|---|---|---|---|
| WO | 2008/085025 A1 | 7/2008 | |
| WO | WO-2021198717 A1 * | 10/2021 | ......... A61B 1/00156 |

* cited by examiner

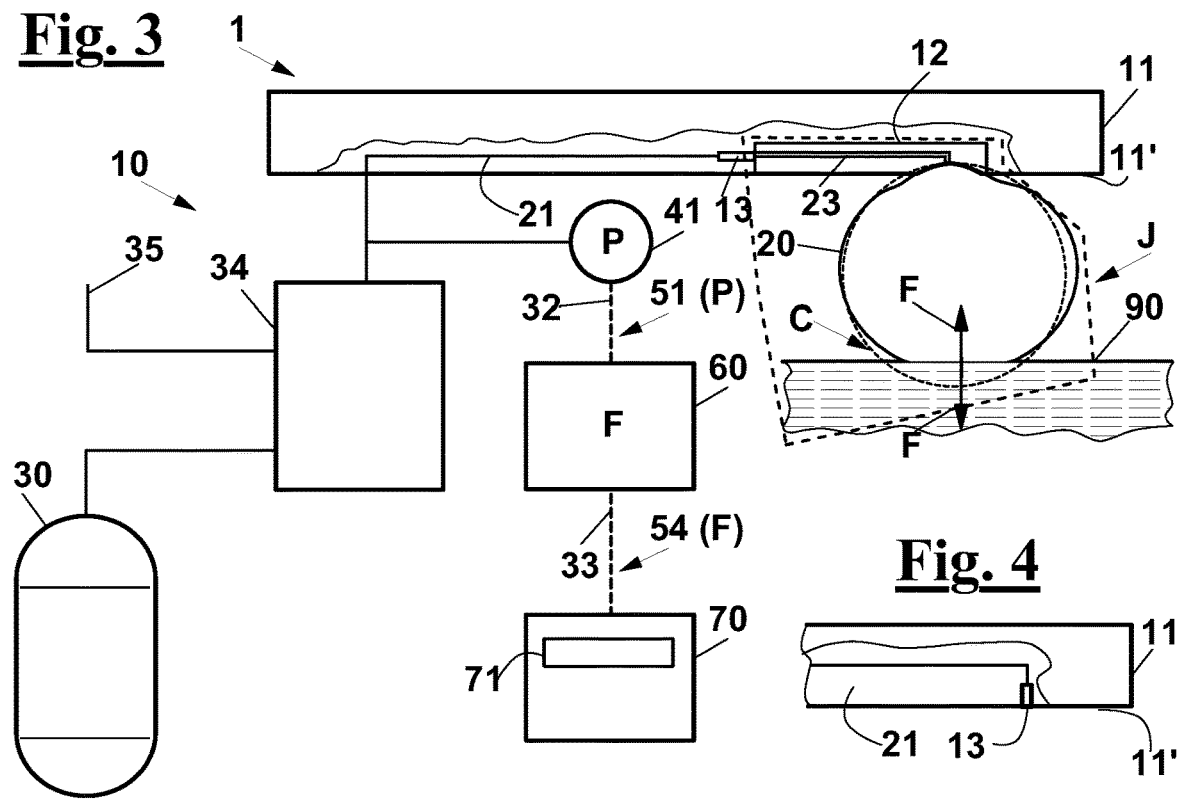
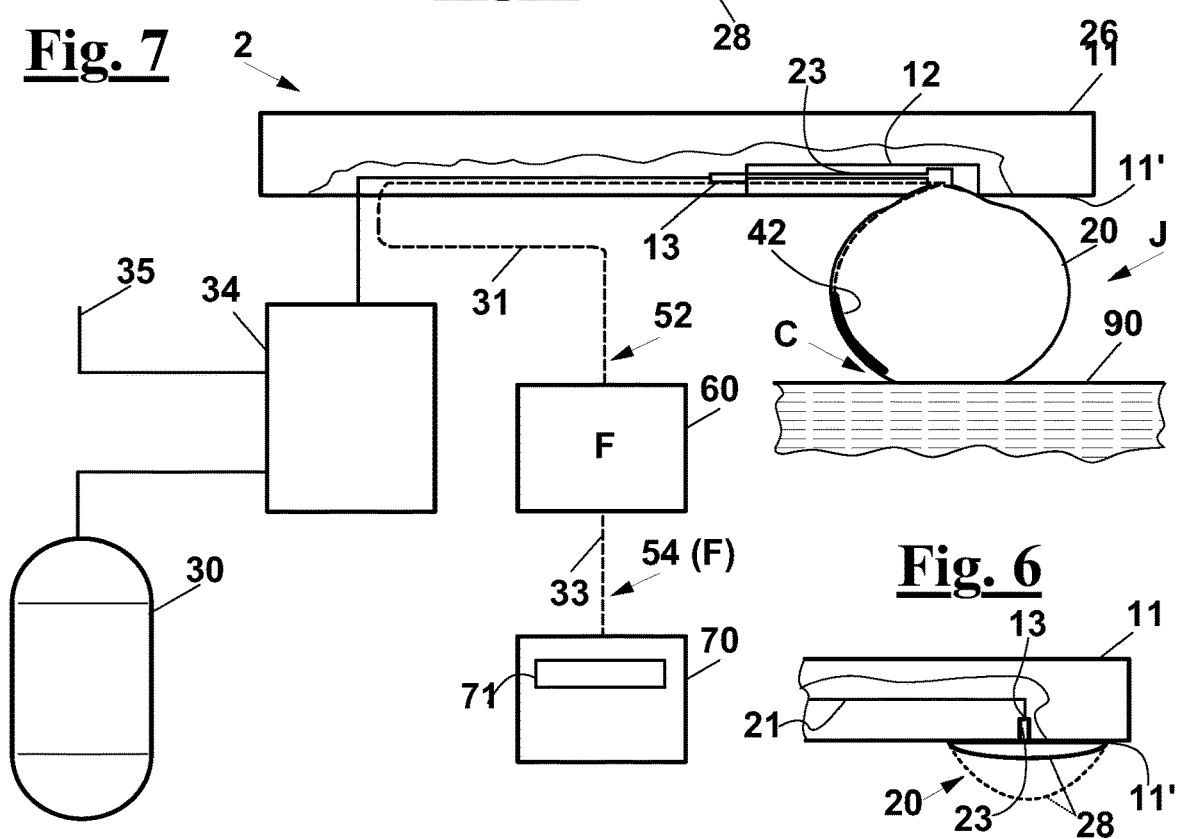

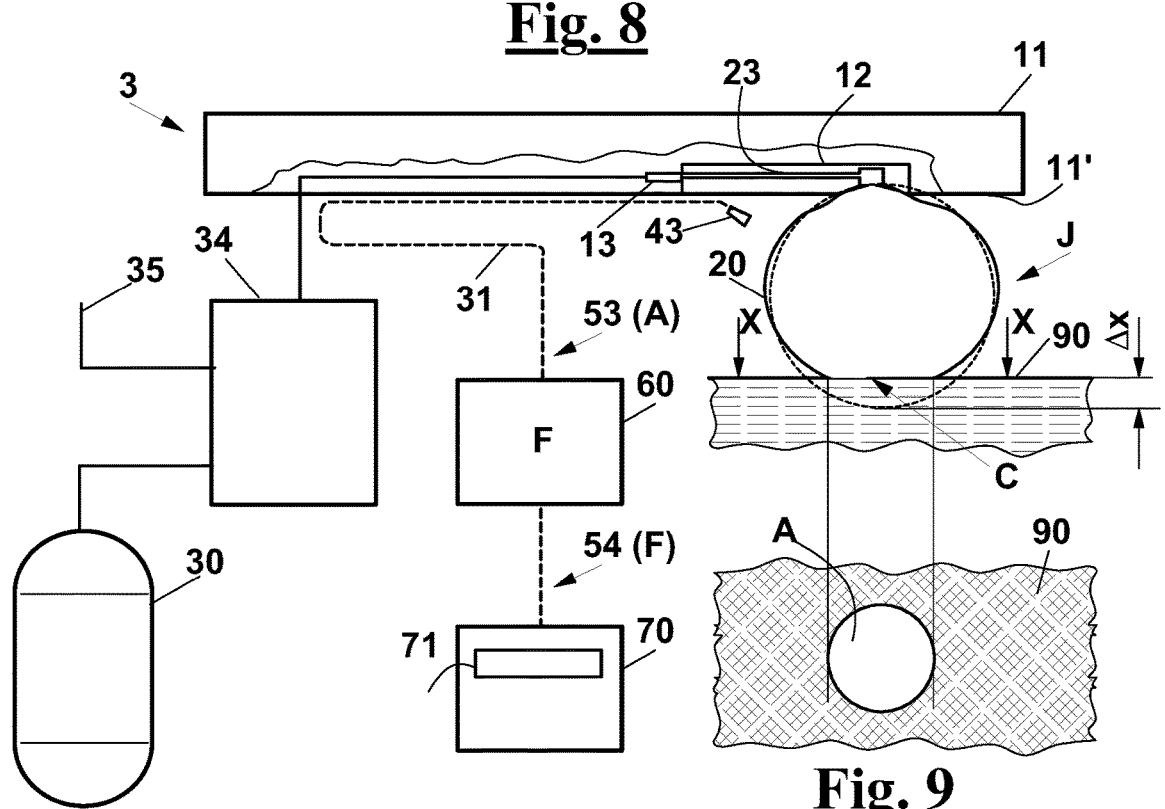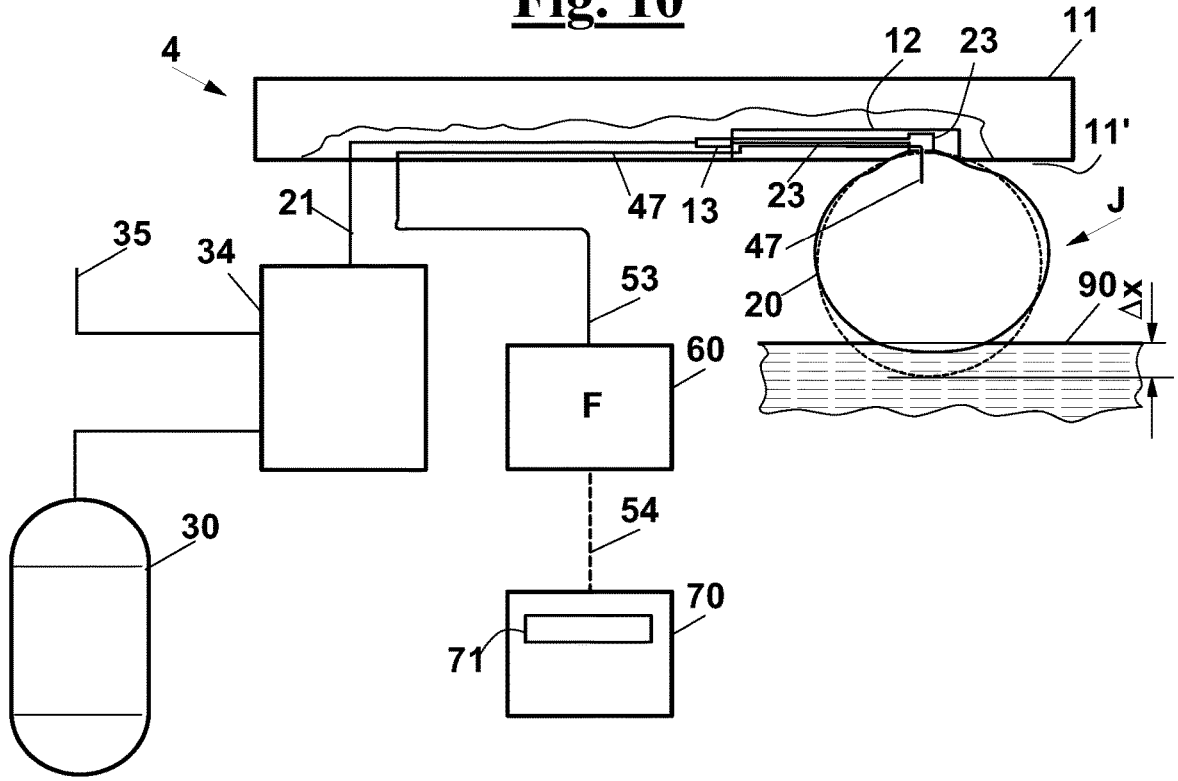

Fig. 19
Fig. 20
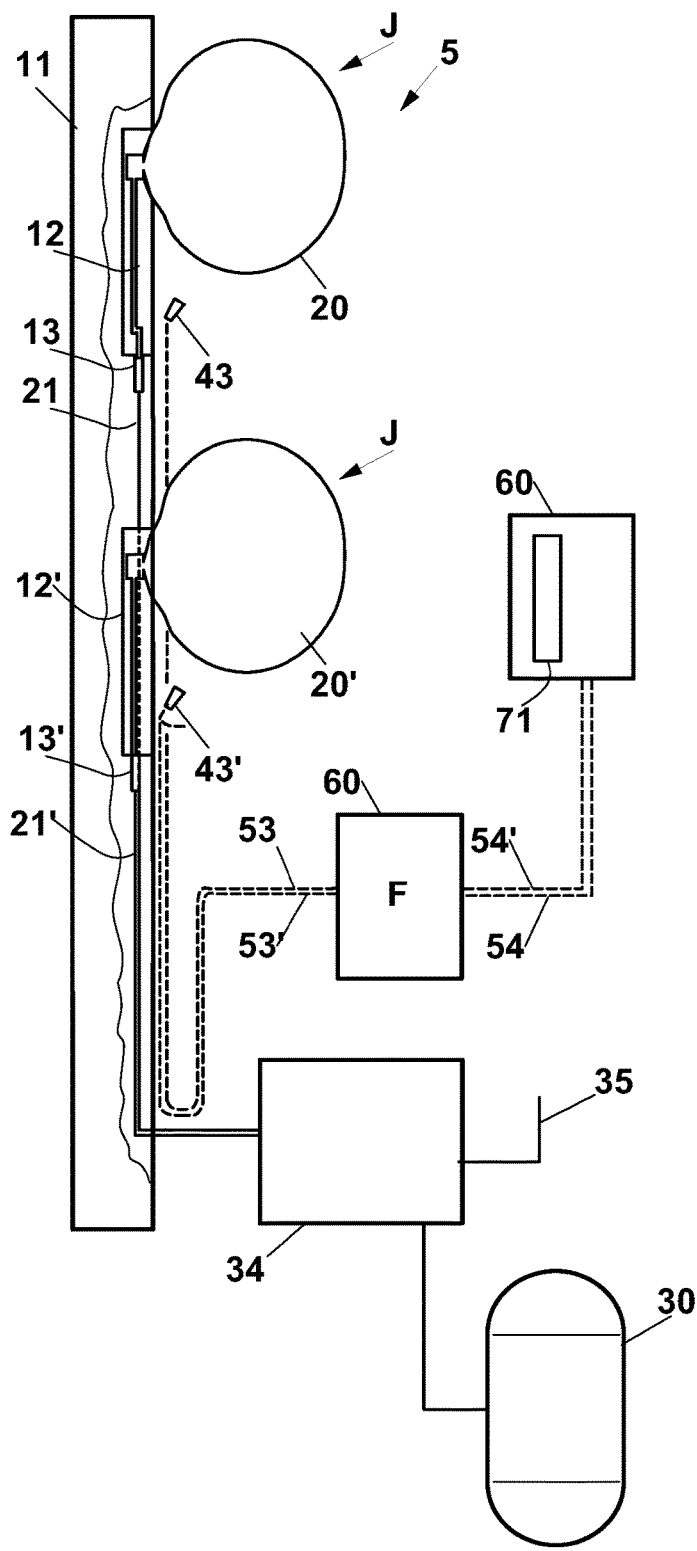
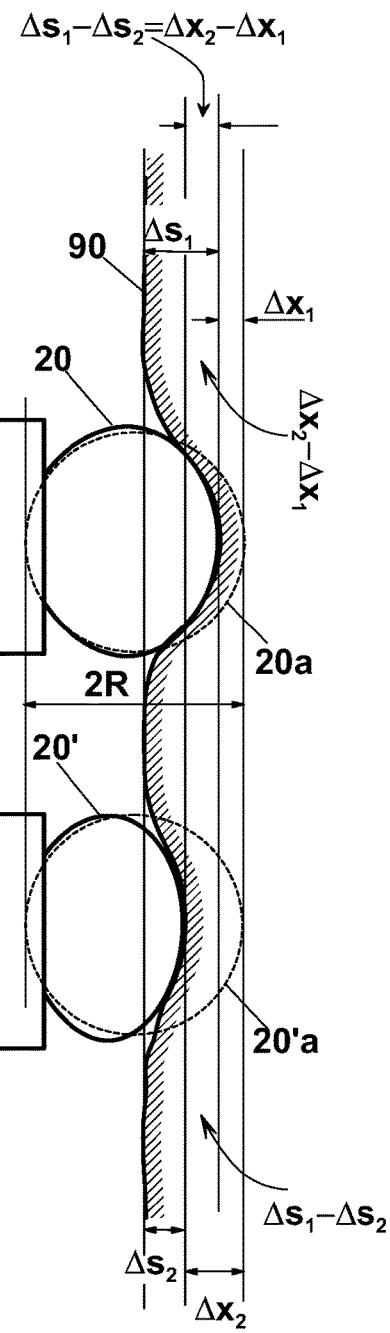

INSTRUMENT COMPRISING A CONTACT FORCE SENSOR DEVICE

FIELD OF THE INVENTION

The present invention relates to a sensor for measuring a force exchanged between the sensor itself and a wall, or a surface of an object upon mutual contact thereof.

The sensor can be advantageously used in a minimally invasive instrument also including a diagnostic, therapeutic or surgical tool, in order to preliminary evaluate the compliance of tissues at an operation region of a patient's body, in particular, in robotic surgery.

Moreover, the sensor can be advantageously used in such fields as remote or segregated manipulations of objects for research or manufacturing purposes, in particular it can be usefully integrated in a robotic hand.

BACKGROUND OF THE INVENTION—TECHNICAL PROBLEMS

Robotic procedures are known in which an operator such as a surgeon or a physician introduces a robotic arm into a patient's body through a small entry site in order to carry out a mini-invasive diagnostic, or therapeutic or surgical operation. The operator controls the robotic arm from outside the patient's body. The robotic arm includes a surgical or diagnostic end-effector, and normally also an endoscope, whose operation is remotely controlled by the operator. A limitation of these procedures resides in that, even if the operator can see the operation region through the endoscope, he/she cannot feel the tissues involved in the operation, and cannot therefore obtain data about their consistency. These data are important to understand the nature of some singularities of the tissues, for example when assessing the presence of a tumour, and/or to preliminary decide if a surgical/diagnostic tool will have to handle the investigated tissue gently, i.e., without exceeding determined contact force threshold values, to prevent damages. Similar problems arise also in the other possible non-medical applications.

The need is therefore felt of providing a surgical or diagnostic instrument with a contact force sensor device that can measure the contact force between the sensor itself and a wall, which can be the wall of a tissue or of an organ in a patient's body, by feeling this wall at given position(s). Such an instrument should also be able to notify the result of the contact force measurement to an operator such as a surgeon or a physician, or even a research or manufacture operator, preferably in the form of a tactile feedback signal, when he/she feels the wall through the contact sensor.

Even if devices are known to provide a tactile feedback to an operator, measuring a contact force within a patient bod is still a troublesome issue.

Firstly, most conventional force sensors are too bulky to be advantageously associated to a surgical or diagnostic tool i.e. end-effector for a mini-invasive procedure. In facts, the size of a mini-invasive surgical access should not exceed 10 to 12 mm.

Moreover, currently available force sensors include electronic parts that do not tolerate the severe sterilization conditions (high temperature, pressure, humidity) that are required in the case of reusable medical devices. On the other hand, the high cost of the endoscopic devices discourages their use as disposable devices, which would be economically unsustainable.

WO 2008/085025 A1 discloses a laparoscopic grasping instrument comprising upper and lower jaws, a liquid-containing balloon frontally protruding from at least one jaw and hydraulically connected to a force sensor so as to transmit a hydrostatic pressure prevailing in the balloon to the force sensor.

US 2010/022918 A1 discloses a surgical manipulator in which a support consists of a plurality of longitudinally arranged, mutually articulated, flat support elements, on both side of which inflatable membranes are arranged. The support is suitable for introduction into a gap between a patient's tissues, in particular brain tissues, so that, by sequentially inflating the membranes of each support after introduction, spacing-apart forces are applied to the tissues forming the gap, which are spaced apart and the device can deeper and deeper penetrate between the tissues. This can be useful for creating a path for diagnostic or surgical instrument between the spaced-apart tissues. The manipulator has a sensor for measuring the pressure of the fluid and a device for determining the compression force produced on the membranes, when arranged within the gap, starting from the measured pressure and from the volume of fluid present in the membrane. Such a device cannot be used for feeling the consistency of tissues as indicated above, because it cannot adjust the inflate gas pressure so finely as required for feeling tissues of different compliance. Severe hazard could be generated, in particular, if this device were used to assess the consistency of a pathological blood vessel, in particular, in the presence of aneurysms or the like.

US 2013/0197493 A1 discloses a minimally invasive instrument in which an enlargeable sensor head includes a resilient flat element comprising a film i.e. membrane element formed by spaced apart first and second layers, between which expansion-sensitive, polymer based resistance elements are arranged transversally with respect to the membrane element.

US 2013/0190688 A1 discloses a catheter at a distal end of which a sponge-like or cushion-like elastic deformation body i.e. a membrane is arranged including electrically, mechanically or optically acting measuring means for detecting a pressing force exerted on the membrane. In an embodiment, strain gages are arranged radially from a center of the deformation body, i.e. radially to the membrane. In another embodiment, a light source is arranged at a center of the deformation body emitting all around, and solar cells are arranged internally to the membrane thereof, so as to detect differentially damped light from to different cells as an effect of a deformation of the membrane due to a contact force acting outside of it.

Other devices are described in US 2017/333125 A1 and in US 2017/340236 A1.

SUMMARY OF THE INVENTION

It is an object of the present invention to provide a contact force sensor device that can be easily associated to a surgical or endoscopic tool to form an integrated instrument suitable for mini-invasive introduction into a patient's body, through a small surgical access.

It is also a feature of the invention to provide such a contact force sensor device that can be manufactured at a low cost, to allow an economically sustainable disposable use thereof.

It is also a feature of the invention to provide such a contact force sensor device in which the electronics can be easily separated from the parts intended for introduction into the patient's body, in order to treat the latter under severe sterilization condition, so that the contact force sensor device can be advantageously integrated with reusable endoscopic instruments.

It is a further object of the invention to provide such a contact force sensor device that can measure the compliance of a tissue within a patient's body, or, more in general, in a remote body.

These and other objects are achieved by an instrument according to claim 1. Advantageous exemplary embodiments of the invention are defined by the dependent claims.

According to the invention, an instrument comprises a support member having a lateral surface, and a contact force sensor device that is integrated in the support member, the contact force sensor device including:

a gas-inflatable balloon, preferably made of latex, arranged to switch between a deflated state, and an inflated state at an inflation pressure and arranged to protrude from the lateral surface of the support member when in the inflated state, said instrument comprising:

a feed duct arranged to feed a gas to the gas-inflatable balloon through a connection member engaged by an entrance portion of the gas-inflatable balloon;

an inflation/deflation valve assembly arranged to selectively connect the gas-inflatable balloon with a gas source or with a gas-discharge vent, respectively, through the feed duct;

a detector configured to output a detection signal responsive to a contact force-related value related to a contact force acting on the gas-inflatable balloon when the gas-inflatable balloon is in the inflated state and is in engaged in a contact with a wall of a body outside of the support member;

a processing unit configured to:
receive an inflate input signal from a user;
upon receiving the inflate input signal, cause the inflation/deflation valve assembly to inflate the balloon to the inflated state;
receive the detection signal and compute a contact force signal responsive to the detection signal according to a predetermined function;
wherein the function is a relationship between the contact force and the force-related value selected from the group comprised of:
the contact pressure;
a deformation value of the gas-inflatable balloon;
a modification of a stretch condition of the membrane, and generated when the gas-inflatable balloon is in contact with the wall,
receive a deflate input signal from the user;
upon receiving the deflate input signal, deflate the gas-inflatable balloon to the deflated state, a contact force-value notification device configured to receive the contact force signal from the processing unit and to notify to a user the contact force signal responsive to the contact force.

With respect to WO 2008/085025 A1, the gas inflatable balloon according to the invention, when inflated with gas, would protrude from the lateral surface of the support, and its inflation pressure $P_0$ can be selected as function of the kind of body to be inspected (for example a tumor, the wall of a body tissue, etc.), which is sided by the support in such a way that the balloon emerges laterally and pushes against the body wall.

The possibility to deflate the balloon has the effect of limiting the force measurement when necessary in order not to stress the body. In fact, it is important that the force reaction of the body wall is measured, but at the same time that the reaction force of the balloon is interrupted at the end of the measurement.

This way, the force measurement would stress the body wall sided by the support only during the measurement, and, as soon as the measurement is completed, the balloon is deflated by backflow of gas. By the invention, therefore, the entity of force measurement is controlled, and this is particularly relevant when a body wall could bear unknown reaction force and compliance as well minimally invasive measurements are required.

In an exemplary embodiment, a surgical or diagnostic tool is arranged at a distal end portion of the support member, and the connection member, engaged by the gas-inflatable balloon through the entrance portion, is arranged at a predetermined distance from the distal end portion. In particular, the instrument can be a robotic surgical and/or diagnostic instrument comprising such a surgical tool as a scalpel, a forceps, a surgical file, and the like, or a diagnostic tool, the surgical and/or diagnostic tool arranged at the end portion of the support member of the instrument.

This way, the instrument can be used during robotic surgical/diagnostic treatment in order to know the value of the forces exchanged between a surgical/diagnostic tool and a patient's tissue or organ under surgery, or an area close thereto.

Using such an instrument, during a diagnostic, surgical or therapeutic treatment, a surgeon or physician can measure the contact forces between the gas-inflatable balloon and the tissue or organ, obtaining useful data about it. Thanks to the selectively inflatable/deflatable balloon, no additional or larger entry site into the patient's body is necessary than the entry site required for the surgical tool to reach the treatment region within de patient's body. The size of the required access to the patient's body for both treatment and tissue investigation purposes can be therefore contained within a minimum value, e.g. about 1 cm.

In fact, in the invention, a gas-inflatable balloon is used as an element sensible to the contact with a tissue. The balloon can be inflated and therefore expanded once the instrument has been introduced in the patient's body and brought to the treatment region. Moreover, the balloon can be maintained in the inflated state only as long as it is required to measure the force, and at the end of the measurement it can be deflated and therefore reduced to a minimum encumbrance state. This way, the sensor does not disturb subsequent diagnostic or surgical treatment performed through the instrument.

More in detail, in the case of a surgical instrument, the surgeon usually requires data that can be obtained by feeling the tissue to be operated in order to evaluate its consistency. For instance, it can be important to feel the consistency of a blood vessel in order to assess the presence of deposits inside it, or the consistency of tissue regions corresponding to anomalous radiographic spots, in order to clarify whether abscesses, tumour masses, or the like, are present. To this purpose, the surgeon brings the instrument to the region to investigate, inflates the balloon to the inflated state so that the balloon comes into contact with a tissue of interest, and receives useful contact force data.

At the same time, the portion of the sensor that calculates and outputs the detection signal can be arranged outside the patient's body. Therefore, only small components must be brought to the treatment region in order to measure the contact force, which is essential to make a mini-invasive instrument.

After measuring the contact force and assessing the condition of the tissues, the surgeon deflates the gas-inflatable balloon to its deflated state, at which it subsequently remains without any hindrance for a possible subsequent surgical or diagnostic procedure carried out by the instrument itself.

This will be described more in detail hereinafter for various exemplary embodiments of the invention configured as a surgical instrument, or a diagnostic instrument, or the like.

The contact force sensor device can be easily manufactured in small dimensions, which enables its integration in a large number of surgical/diagnostic instruments, typically in more or less common robotic surgery instruments.

The gas used to inflate the gas-inflatable balloon can be air, but any biologically compatible gas can be used if required.

The processing unit operates as a transducer, i.e., it is configured to correlate a contact force acting between the inflated balloon and a tissue and a contact force-related quantity i.e. value, which is modified when the balloon comes into contact/is removed from the contact with the tissue.

As detailed hereinafter, this quantity can be the inner pressure of the gas-inflatable balloon, more precisely the pressure increase that occurs as an effect of said contact. In this case, the pressure is detected by a pressure sensor pneumatically connected with the inside of the balloon. As an alternative, the above-mentioned quantity can be an optically-detected change of dimension of the balloon that occurs as an effect pf the contact. As a further alternative, the quantity can be the variation of a stress value that takes place in the membrane of the gas-inflatable balloon upon contacting the tissue, which can be detected by means of a strain gage.

In particular, the instrument comprises an engagement portion arranged to engage with a robotic arm, and the processing unit is configured to send the contact force signal to a drive unit of the robotic arm.

Advantageously, the processing unit is configured to output a drive force limitation signal according to the value of the contact force or of the compliance, and is also configured to automatically modify the force exerted by the surgical instrument on the tissue responsive to the measured contact force or compliance, by reducing the force of the instrument if the compliance is lower than a predetermined value.

Preferably, the support member comprises a recess, and the connection member is arranged within the recess, the gas-inflatable balloon and the recess arranged in such a way that the gas-inflatable balloon is contained within the recess when in the deflated state, and protrudes from the recess when in the inflated state.

This way, the encumbrance of the gas-inflatable balloon at its deflated state can be contained at most, further simplifying introduction of the instrument through a mini invasive entry and further reducing hindrance during a possible surgical or diagnostic operation.

Advantageously, the gas-inflatable balloon comprises a rigid back portion configured to lay on the lateral surface of the support member, and an inflatable front portion opposite to the rigid back portion, wherein the entrance portion protrudes from the rigid back portion and has an engagement means to engage with the connection member. This solution simplifies the operations of applying/detaching the gas-inflatable balloon on/from the support member, which is frequently required in the case of a reusable instrument.

In an exemplary embodiment, the gas-inflatable balloon, or a surface portion thereof has a plurality of markers, and the detector is an image detector arranged to "observe" the gas-inflatable balloon, or a surface portion thereof, i.e. to detect an image of the gas-inflatable balloon and of the markers, so as to detect a modification of the markers due to a contact of the gas-inflatable balloon in the inflated state and a wall;

output an image signal as the detection signal;

moreover, the processing unit comprises:

an image-processing means configured to identify the modification of the markers in the image signal and to calculate the force-related deformation value of the gas-inflatable balloon due to the contact, as the force-related value related to the contact force;

a force-computing means configured to compute the contact force signal comprising force values responsive to the force-related deformation value according to the predetermined function.

The image detector can have the form of an optical-fibre terminal located proximate to the gas-inflatable balloon, and is arranged to measure a deformation of a surface portion of the gas-inflatable balloon, i.e. it can have an arrangement as described hereinafter. This way, only passive electronic-free components are introduced into the patient's body. This is useful in the case of a reusable instrument, since these parts can be sterilized under severe conditions, as required, without being damaged or, as an alternative they can be disposed without any cost issues.

In particular, the image detector can be arranged at a position outside of the gas-inflatable balloon. For instance, in a surgical or diagnostic instrument the image detector can be provided by an optical device mainly used for monitoring a surgical or diagnostic procedure. As an alternative, the image detector can be arranged at a position inside the gas-inflatable balloon, in particular, proximate to the entrance portion, more in particular it can be inserted into the gas-inflatable balloon through its entrance portion.

The modification of the markers that the image detector can detect can be a modification, e.g. a shape change, with respect to a rest arrangement of the markers, or it can be a displacement of the markers with respect to the position they have before the contact takes place, with respect to the support of the instrument, and responsive to the initial inflation gas pressure. This way, from the displacement or the shape change of the markers as detected by the image detector, the amount of the gas-inflatable balloon deformation can be established when the latter comes into contact/is removed from contact with the wall, e.g. the tissue of the patient's body. If the original shape and a stress-strain relationship of the gas-inflatable balloon are known for a given inflate pressure, the force due to the contact with the tissue can be estimated by the force-computing means of the processing unit.

In particular, the plurality of markers comprises a plurality of reference points, and the processing unit is configured to:— starting from the image signal, count a number of the reference points that disappear, due to the contact, from a portion of the image in the image signal;

calculate the force-related deformation value from the number of disappeared reference points.

In particular, the force-related deformation value of the gas-inflatable balloon can be a flattening length due to the contact or, as an alternative, a contact surface area created by the contact.

The determination of the contact force through a deformation optically measured by imaging of the gas-inflatable balloon is very easy. Moreover, most conventional surgical and diagnostic systems include optical microscopes and video cameras are already provided, in particular, in the form of optical fibres, which promotes integration of the contact force sensor device in such conventional systems or instruments. In some instances, as in the case of the endoscopes, the optical devices are the main components of the instrument.

Accordingly, in an exemplary embodiment of the invention, an endoscopic video camera is arranged at the end portion of the support member. In other words, the contact force sensor device can be incorporated in an instrument configured to perform both tactile and visual detection of tissues and organs that are involved in a surgical or diagnostic operation, or are present next to the operation region.

In another exemplary embodiment, the detector is a pressure detector arranged to:
detect the contact pressure, as the contact force-related value, between the inflation/deflation valve assembly and the gas-inflatable balloon when the gas-inflatable balloon is contact with the wall;
output a pressure signal as the detection signal;
and the processing unit is configured to:
compute the contact force signal comprising force values responsive to the contact pressure value according to said predetermined function.

Even in this case, only passive electronic-free components are introduced into the patient's body, which is useful for reusable instruments, since these parts can tolerate the required severe sterilization conditions, as required.

Moreover, the embodiment according to this exemplary embodiment is advantageous since it uses a pressure detector to produce a detection signal, i.e. it uses an item that is in any case required to control the inflate pressure of the balloon, without requiring any further detection system, thus simplifying the instrument. It only requires adaptation of the processing unit to treat the pressure detection signal as a contact force-related value, as described hereinafter. Moreover, a pressure-based contact force measurement does not require introducing such additional components into the patient's body as special cabling or resistive, electrically supplied devices.

Therefore, the instrument according to this exemplary embodiment fully complies with the size restrictions imposed by minimally invasive surgery, since the pressure sensor can be arranged at a position remote from the gas-inflatable balloon, for instance, it can be housed within a robotic arm holding the instrument, or in any case outside of the patient's body.

For example, the processing unit is configured to calculate an excess pressure value $\Delta P$ equal to the difference between the contact pressure and the inflation pressure of the gas-inflatable balloon, and the function is a polynomial function of the type:

$$F = a \cdot \Delta P - b \cdot \Delta P^2, \quad [1]$$

wherein a and b are parameters depending on a material and on a thickness of a membrane of the gas-inflatable balloon, and, for a given gas-inflatable balloon, on the inflation pressure, as it can be easily computed by a calibration procedure to be carried out for a give gas-inflatable balloon.

Preferably, the processing unit is configured to:
calculate a plurality of values of an energy amount received by the instrument upon the contact between the gas-inflatable balloon and the wall at different values of a couple of deformation parameters of the gas-inflatable balloon, the energy comprising an energy portion associated to a deformation of the gas-inflatable balloon and an energy portion associated to a compression of the gas within the gas-inflatable balloon, due to the contact;
calculate a relationship between the deformation parameters based on an equation of state of the gas, so as to obtain the values of the energy amount as a relationship with only one deformation parameter of the deformation parameters;
calculate the contact force as a product between the contact pressure as a relative pressure and contact surface area of the gas-inflatable balloon and the wall.

This way, no calibration procedure, possibly periodically repeated, is required, which remarkably simplifies the use of the instrument.

In a further exemplary embodiment, the detector is a strain gage integrally arranged along a surface of a membrane of the gas-inflatable balloon, the strain-gage configured to
detect the modification of a stretch condition of the membrane due to a contact/end of a contact of the membrane, previously inflated to the inflated state, and a wall;
output a strain signal responsive to the modification of the stretch condition, as the detection signal,
and the processing unit is configured to compute the contact force signal comprising force values responsive to the strain signal according to a predetermined function.

The instrument according to this embodiment has the advantage that a detection signal is provided that is easier to correlate to a force acting on the membrane.

In particular, the strain gage can lay on a surface of the membrane, in particular it can lay on the internal surface thereof, or can be arranged at a position embedded in the membrane of the gas-inflatable balloon. The latter solutions are safer in terms of separation of an electrically supplied component from the inner of the patient's body.

In a further exemplary embodiment, the contact force sensor device also comprises:
at least one second gas-inflatable balloon arranged to switch between a deflated state, and an inflated state, and arranged to protrude from the support member when in the inflated state
a second feed duct arranged to feed a gas to the second gas-inflatable balloon through a second connection member engaged by a second entrance portion of the second gas-inflatable balloon;
and the inflation/deflation valve assembly is arranged to selectively connect the second gas-inflatable balloon with the gas source and with the gas-discharge vent through the second feed duct, and
the detector device is configured to output also a second detection signal according to a force-related value related to a second contact force acting on the second gas-inflatable balloon, and the processing unit is configured to:
receive the second detection signal;
compute and output also a second contact force signal according to the predetermined function.

In a particular exemplary embodiment, the instrument can be configured to measure a compliance parameter of the wall the gas-inflatable balloon comes into contact with. In this particular exemplary embodiment, the inflation/deflation valve assembly is arranged to inflate the first and second gas-inflatable balloons up to respective initial pressures different from each other such that the first and second gas-inflatable balloons have respective initial radiuses equal to each other; and the processing unit is configured to compute a compliance parameter of an environment outside the first and the second gas-inflatable balloons, e.g. a wall, according to the formula:

$$Ks = \frac{F1 - F2}{\frac{F_2}{\pi P_{o2} R_2} - \frac{F_1}{\pi P_{o1} R_1}} \quad [2]$$

where
$F_1$ and $F_2$ are forces obtained from the first and second contact force signals, respectively;
$P_{o1}$ and $P_{o2}$ are the measured initial gas pressure values within the first and second gas-inflatable balloons, respectively;
moreover, the processing unit is configured to generate a compliance signal according to the calculated compliance parameter, and the contact force-value notification device is configured to receive and to notify the compliance signal to the user.

The detector can be any of the previously described ones, i.e. a pressure detector, an image detector, as well as a strain gage, provided the processing unit is specialized thereto.

In an exemplary embodiment, the contact force sensor device, which is integrated in the support member, includes at least one of:
the feed duct;
the detector;
the processing unit;
the contact force-value notification device;
a combination thereof,
integrated in said support member (11).

This further improves simplicity of use of the instrument.

Advantageously, the instrument is associated to a haptic interface equipped with vibrotactile actuators. In particular, the instrument can comprises a handle portion, and the contact force-value notification device comprises an actuator, for example a vibrotactile actuator, arranged at the handle portion, in order to provide the contact force signal to the user in the form of a tactile feedback. This enables the operator to perceive the measured force directly on his/her own hands.

Apart from surgical and diagnostic applications, the contact force sensor device of the invention can be advantageously used for a wide range of remote manipulation operations. In particular, a device like a robotic hand including the above described contact force sensor device can also comprise at least one robotic finger arranged at the end portion of the support member, the robotic finger having a fingertip portion, in a distal phalanx member, at which the gas-inflatable balloon it is arranged. In particular, the instrument can comprise a plurality of fingers that are arranged to form a robotic hand. Gas inflatable balloons can be also arranged at any other proximal or medial phalanx member of the robotic finger.

In a further exemplary embodiment of the invention,
the support member comprises a plurality of sequentially arranged phalanx support members that are mutually articulated in such a way to form a robotic finger;
the gas-inflatable balloon is arranged on at least one of the phalanx support members;
the processing unit is configured to provide the contact force signal to a drive unit of the robotic finger such that the drive unit can adjust a grip force of the robotic finger responsive to the contact force.

It falls within the scope of the invention also a robotic hand including a plurality of robotic fingers comprising the instrument described above.

In this case, besides enabling a force measurement, the use of the gas-inflatable balloons between the fingers of the robotic hand and a manipulated object provides a conveniently soft interaction therebetween, provided a correspondently suitable inflate pressure is chosen.

To this purpose, the inflation/deflation valve assembly can advantageously comprise a pressure-adjustment valve configured to adjust the pressure of the gas provided to the gas-inflatable balloon in the inflated state within a predetermined range of values or according to predetermined pressure values. This way, the stiffness of the gas-inflatable balloon in the inflated state can be selected by the operator, which allows measuring contact forces between the gas-inflatable balloon and tissues of different consistency or compliance without damaging them. In the case of a robotic hand and, in particular, for such applications as "robotic forceps", the stiffness of the gas-inflatable balloon can be suitably reduced if the instrument must handle a very delicate object. This way, the design of the robotic hand does not need to be changed, in other words the robotic hand can have a general-purpose stiff structure, since its compliance to the interaction with the objects is established through the inflate pressure within gas-inflatable balloon, and can be adjusted by the software that controls the inflation/deflation valve assembly.

Advantageously, the gas-inflatable balloon and the inflation/deflation valve assembly are configured to create an inflate pressure set between 4 and 12 kPa in the gas-inflatable balloon.

BRIEF DESCRIPTION OF THE DRAWINGS

The invention will be now shown with the description of its exemplary embodiments, exemplifying but not limitative, with reference to the attached drawings, in which like reference characters designate the same or similar parts, throughout the figures of which:

FIGS. 1 to 3 diagrammatically show an instrument according to an exemplary embodiment of the invention, in which the detector is a pressure detector, in a deflated state (FIG. 1), in an inflated state without contact (FIG. 2), and in an inflated state with contact with a wall of a body outside of said support (FIG. 3), i.e. in a —measurement condition, the gas-inflatable balloon in the corresponding initial inflated state being represented in dotted line;

FIGS. 4 to 6 show a portion of the support member of the instrument and a gas-inflatable balloon according to an embodiment thereof;

FIG. 7 diagrammatically shows an instrument according to another exemplary embodiment of the invention, in which the detector is a strain gage, in a force measurement condition, the gas-inflatable balloon in the corresponding initial inflated state being represented in dotted line;

FIG. 8 diagrammatically shows an instrument according to a further exemplary embodiment of the invention, in which the detector is an image detector, in a force-measurement condition, the gas-inflatable balloon in the corresponding initial inflated state being represented in dotted line;

FIG. 9 is a cross sectional view at line X-X of FIG. 8, showing the contact surface between the gas-inflatable balloon and the wall;

FIG. 10 diagrammatically shows an instrument according to a modification of the embodiment of FIG. 8, in which the image detector comprises an optical fibre arranged inside the gas-inflatable balloon;

FIG. 19 diagrammatically show an instrument according to a further exemplary embodiment of the invention, comprising two gas-inflatable balloons, in a modification providing image detectors;

FIG. 20 show an arrangement of the gas-inflatable balloons of the instrument of FIG. 19 in a measurement condition, to explain compliance measurement of a wall;

DESCRIPTION OF PREFERRED EXEMPLARY EMBODIMENTS

Figure 1:
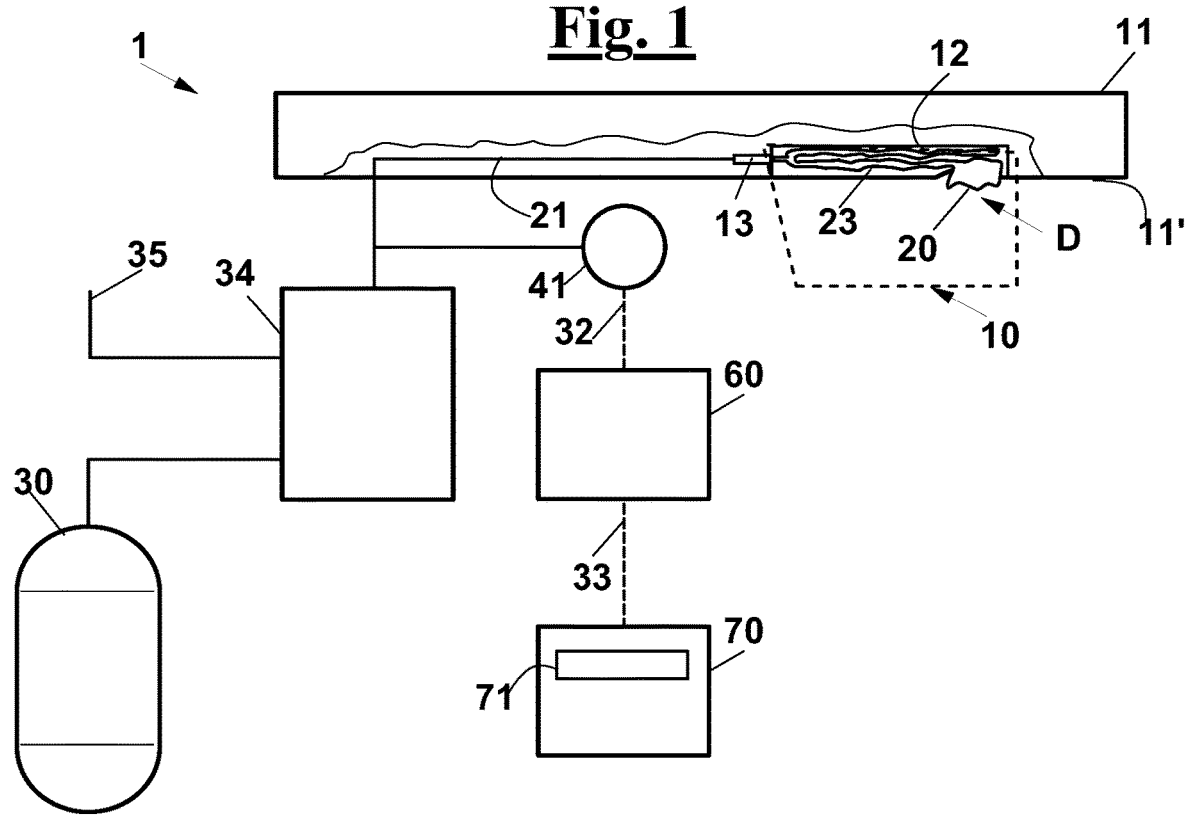
Figure 2:
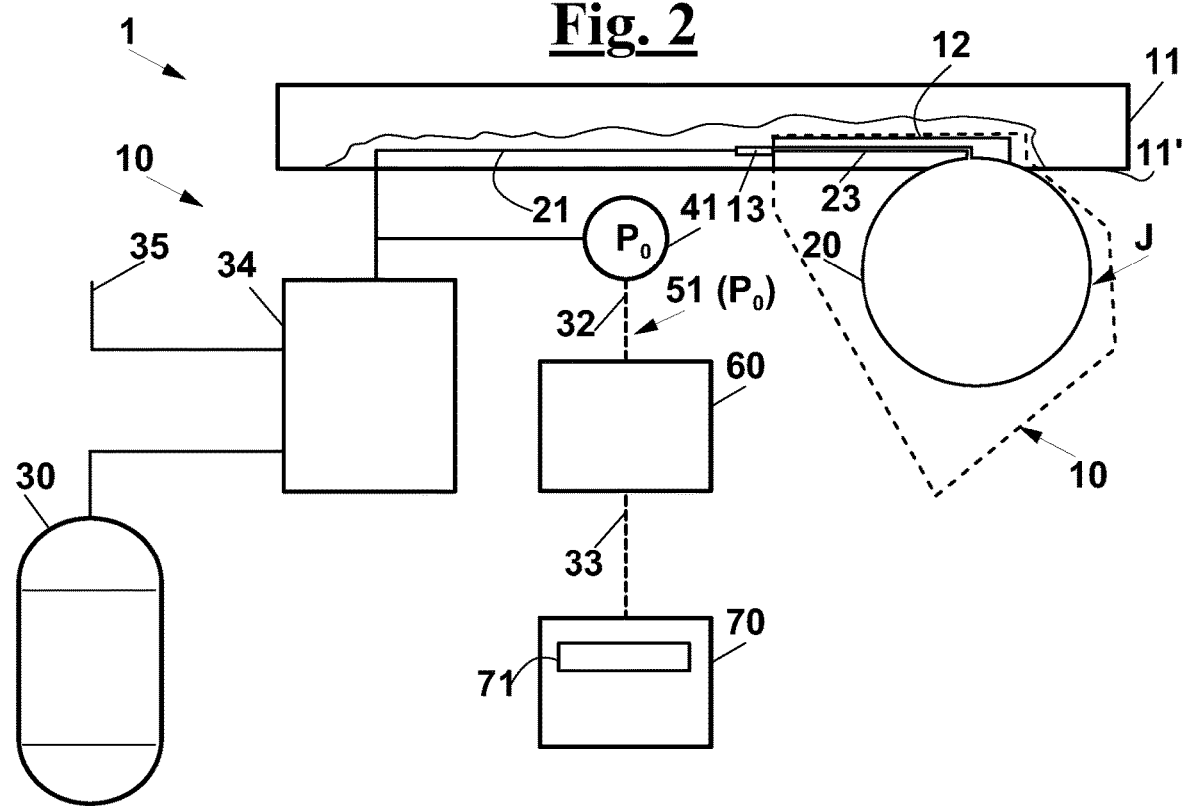

With reference to FIGS. 1 to 3, an instrument 1 is described, according to an exemplary embodiment of the invention, comprising a support member 11 and a contact force sensor device 10 integrated in support member 11. Contact force sensor device 10 serves for measuring a contact force exchanged between a gas-inflatable balloon 20 thereof and a wall 90 of a body outside of support member 11. Gas-inflatable balloon 20 is preferably made of latex, and has an entrance portion 23 by which it is preferably demountably connected to a connection member 13 integral to support member 11. Gas-inflatable balloon 20 is arranged to switch from a deflated state D (FIG. 1) to an inflated state J (FIGS. 2 and 3), in which gas-inflatable balloon 20 protrudes from a lateral surface 11' of support member 11.

Preferably, support member 11 has a recess 12 in which connection member 13 is arranged. In this case, gas-inflatable balloon 20 and recess 12 are arranged in such a way that gas-inflatable balloon 20 is contained in recess 12 when it is in deflated state D (FIG. 1), and protrudes out of recess 12 when it is in inflated state J (FIGS. 2 and 3).

Contact force sensor device 10 also comprises an inflation/deflation valve assembly 34 connected with gas-inflatable balloon through a feed duct 21. Valve assembly 34 is arranged to selectively connect inflation/deflation duct 21 and gas-inflatable balloon 20 with a gas source 30 or with a gas-discharge vent 35, in order to inflate or deflate, respectively, gas-inflatable balloon 20.

In the exemplary embodiment of FIGS. 1-3, a pressure detector 41 of known type is pneumatically connected to gas-inflatable balloon 20 to measure a pressure P inside it. In particular, pressure detector 41 can be pneumatically connected to feed duct 21 at a position thereof between gas-inflatable balloon 20 and valve assembly 34.

Pressure detector 41 is configured to output a detection signal, in this case a pressure detection signal 51 responsive to measured pressure P. In particular, pressure detection signal 51 is a continuous electric signal ranging between predetermined voltage or current minimum and maximum values (conventionally 4-20 mA), corresponding to a minimum value and a maximum value, or vice-versa, of a predetermined pressure range.

Moreover, contact force sensor device 10 comprises a processing unit 60 configured to receive an inflate input signal, not shown, from a user and, upon receiving this inflate input signal, to cause inflation/deflation valve assembly 34 to inflate gas-inflatable balloon 20 to the inflated state J, i.e. up to initial pressure or inflate pressure $P_0$. Processing unit 60 is also configured to receive detection signal 51, for instance via a conventional electrical connection means such as a wire 32, and to calculate a contact force signal 54 responsive to detection signal 51, according to a predetermined function as exemplified hereinafter.

Processing unit 60 is also configured to receive a deflate input signal from the user, and to deflate gas-inflatable balloon 20 upon receiving this deflate input signal, so that gas-inflatable balloon 20 is brought do the minimum encumbrance deflated state. This enables the user to easily withdraw the instrument from the patient's body, or to go ahead with a diagnostic or surgical procedure, in the case of an instrument is equipped with tool intended to this purpose, as exemplified hereinafter.

More in detail, in this exemplary embodiment detection signal 51 is a pressure signal indicating the pressure within gas-inflatable balloon 21, and processing unit 60 is configured to calculate an excess pressure value $\Delta P$ that is the difference between measured pressure P and inflation pressure $P_0$, and to treat excess pressure value $\Delta P = P - P_0$ as a force-related value, i.e. a value related to a contact force F that is exchanged between gas-inflatable balloon 20 and wall 90 (FIG. 3). In other words, contact force F can be calculated as a function of excess pressure value $\Delta P$ by processing unit 60.

The relationship between F and $\Delta P$ depends on some features of gas-inflatable balloon 20, firstly on material, thickness and initial inflate pressure $P_0$. In a particular case, the function or relationship between contact force F and excess pressure ΔP and can have the form:

$$F = a \cdot \Delta P - b \cdot \Delta P^2, \quad [1]$$

in which a and b are parameters depending on initial inflate pressure $P_0$.

This relationship, i.e. the dependence of a,b on initial inflate pressure $P_0$ has been investigated for some gas-inflatable balloons. In particular, for a 15 mm diameter latex gas-inflatable balloon, a calibration process has been carried out by an assembly, not shown, comprising the above gas-inflatable balloon 20 and pressure detector 41 according to the invention, along with a conventional force sensor arranged in parallel to gas-inflatable balloon 20.

The calibration procedure, exemplifying a mode of use of the instrument, consisted in:
inflating gas-inflatable balloon 20 to a given initial inflate pressure $P_{0,1}$;
causing the assembly to interact with a given substrate or wall 90 at various intensities, i.e. pressing more or less the assembly on wall 90; and, for each condition:
measuring force F by the conventional force sensor;
measuring ΔP by pressure detector 41;
repeating up to N times the above steps after bringing gas-inflatable balloon 20 to different respective initial inflate pressures $P_{0,i}$, i=2 ... N, inflate pressures $P_{0,i}$ ranging in a predetermined pressure range, e.g. 4.0÷11.2 kPa;
retrieve relationships between a and $P_0$ and b and $P_0$.

The above procedure lead to the following table.

| Range of initial inflate pressure $P_0$ | a | b |
| --- | --- | --- |
| 4.0 ÷ 5.2 kPa | 1.011 | 0.07959 |
| 5.2 ÷ 6.4 kPa | 1.134 | 0.09369 |
| 6.4 ÷ 7.6 kPa | 1.196 | 0.09798 |
| 7.6 ÷ 8.8 kPa | 1.200 | 0.08410 |
| 8.8 ÷ 10.0 kPa | 1.215 | 0.07959 |
| 10.0 ÷ 11.2 kPa | 1.289 | 0.07959 |

Such a procedure can be repeated for any gas-inflatable balloon.

In an alternative embodiment, processing unit 60 is configured to:
calculate a plurality of values of an energy amount E received by instrument upon contact C between gas-inflatable balloon 20 and wall 90 at different values of a couple of deformation parameters x,R of gas-inflatable balloon 20, energy amount $E = E_d + E_c$ comprising energy portions $E_d$, $E_c$ associated to a deformation of gas-inflatable balloon 20 and to a compression of the gas therein, respectively, due to contact C;
calculate a relationship between deformation parameters x,R based on an equation of state of the gas, so as to obtain the values of the energy amount as a relationship with only one deformation parameter of deformation parameters x,A;
calculate contact force F as a product between contact pressure P as a relative pressure and contact surface area A of gas-inflatable balloon 20 and wall 90.

For example, it is assumed that
the stress-strain behaviour of membrane 22 of gas-inflatable balloon can be described by linear elasticity theory, since the deformations involved are reversible and relatively small;
the shape of gas-inflatable balloon 20, when inflated, is a sphere of radius R, which is known for each any value of inflation pressure P;
wall 90 is stiffer than gas-inflatable balloon 20;
wall 90 is considered to be flat, in the practice it has a radius of curvature much longer than the radius R.

Figure 32:
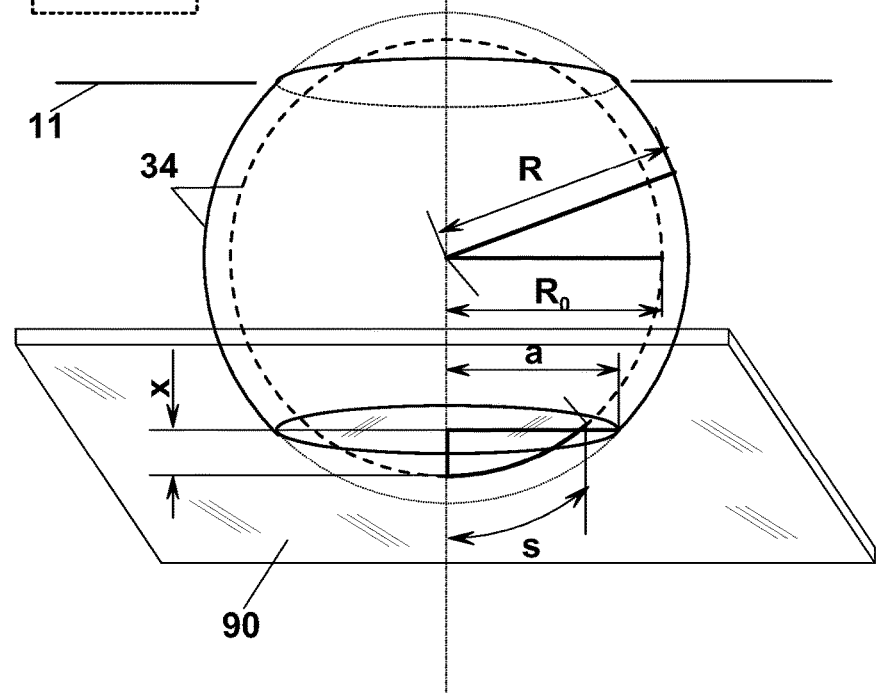
FIG. 32 shows a gas-inflatable balloon according to one embodiment, in an inflated state and in a contact condition.

Gas-inflatable balloon 20 is initially inflated to inflate pressure $P_0$, corresponding to a relative inflate pressure $P_0^R$, to which initial radius $R_0$ of gas-inflatable balloon 20 and thickness h of membrane 22 are proportional. Due to contact C, the shape of gas-inflatable balloon 20 changes as shown in FIG. 32, the pressure and the contact radius increasing from initial inflate values $P_0, R_0$ to contact values $P_0, R_0$, respectively, while two equivalent contact flattened circular areas A are formed at both poles of gas-inflatable balloon 20. Since internal pressure is equally distributed in the whole circuit, contact force F is:

$$F = p^R \pi a^2 \quad [3]$$

where a is the radius of contact areas A and $P^R$ is the relative pressure corresponding to contact pressure $P^R$. Defining as x, contact radius a is $(R^2 - (R_0 - x)^2$. Since $P^R$ is measured, the only unknowns are x and R.

Deformation energy $E_d$ can be written $E_d = E_{ds} + E_{db}$, where $E_{ds}$, $E_{db}$ are stretching and bending contributions, respectively. The stretching energy can be written $$E_{ds} = \int_{2\theta} \sigma \varepsilon dS \quad [4]$$

where ε is the two-dimensional strain tensor, a is the two-dimensional stress tensor, and the integration is over the surface of gas-inflatable balloon 20. It can be as assumed that the volume of membrane 22 itself ($4\pi R^2 h$) remains essentially constant, so thickness h of membrane 22 can be expressed as $h = (h_d R_d^2)/R_0^2$, where $R_d$ and $h_d$ are the radius and the thickness of deflated membrane 22. It is supposed that h remains constant during compression. Since the membrane 22 is isotropic and spherical, $\alpha = (E\varepsilon)/(1-v)$.

Stretching energy $E_{ds}$ is assumed to be the sum of the contribution of the spherical caps turned into flat contact areas A and of the rest of the spherical surface. Defining as s half the length of the cap's arc, the strain is $\varepsilon = (a-s)/s$. To simplify the computation, s can be approximated to the chord $\sqrt{2R_0 x}$. Apart from the spherical caps, membrane 22 stretches increasing radius R of the sphere. The resulting stretching energy is therefore $$E_{ds} \sim \frac{4Eh\pi}{(1-v)}\left[\left(\frac{R-R_0}{R_0}\right)(R_0^2 - R_0 d) + \left(\frac{a-s}{s}\right)^2 R_0 d\right] \quad [5]$$

At a same contact force F, higher pressure gas-inflatable balloon 20 is subject to a smaller indentation, and thereby contact area A is smaller. Thus, if inflation pressure $P_0$ is higher than a predetermined threshold, it can be assumed that gas-inflatable balloon 20 maintains a spherical shape. If $P_0$ is smaller than this threshold, the contribution of final flat surfaces A to stretching energy $E_{ds}$ is not negligible any longer. In this case, large contact areas A are supposed to be given from the stretching of the spherical caps.

Bending energy $E_{db}$ is negligible for a thin membrane, except proximate to the edge of contact area A. An estimation of $E_{db}$ can be made by $E_{db}$ treating membrane 22 based on beam theory. Therefore, $$E_{db} = \frac{EI}{2}\frac{hL}{\rho^2} \qquad [6]$$

where $I=h^3/12$ is the second moment of area of 'beam' cross-section, $L=2\pi a$ is the length of the contact circle, and p is the local radius of curvature, of order $h/\theta$, with $\theta$ the contact angle. Manipulating the latter relationship and approximating $\theta \approx \sin\theta = a/R$, the bending energy is $$E_{db} = \frac{Eh^2\pi}{12}\frac{a^2}{R^2} \qquad [7]$$

Concerning compression energy $E_c$, the gas is assumed to be ideal, therefore $$E_c = -\int_{V_0}^V PdV = -\int_{V_0}^V \left(\frac{P_0V_0}{V} - P_a\right)dV = P_0V_0\ln\frac{V}{V_0} + P_a(V - V_0) \qquad [8]$$

with $V_0$ and V the volume of the whole circuit (gas-inflatable balloon 20 and piping including at least feed duct 21) before and after contact C, respectively. $V_0$ is therefore the sum of piping volume $V_c$, and of volume of the sphere of radius $R_0$, defined as $V_{s0}$. Once contact C established, gas-inflatable balloon 20 is a sphere of radius R (Vs), without two symmetrical spherical caps. Thus, $V=V_c+V_s-2\pi H^2(R-H/3)$, where $H=x+\Delta R$ is the height of the spherical cap. Pressure variation involves the whole pneumatic circuit. Hence, the contact geometry cannot be described by looking only at a close neighbourhood of the contact surface. However, $V_c$ is a constant value and it should be computed once for every identical systems.

Contact force F can be computed as total reaction force, according to Castigliano's theorem, and therefore $$F = \frac{\partial}{\partial(2x)}(E_{ds} + E_{db} + E_c) \qquad [9]$$

where the unknowns are the deformation x and the new incremented radius R. To find a relationship between them, the ideal gas law can be used $$V_c + V_{s0} = \frac{P}{P_0}\left[V_c + V_s - 2\pi H^3\left(R - \frac{H}{3}\right)\right] \qquad [10]$$

obtaining R as a function of x. Then, equalizing [9] to [3] an equation is obtained in which x is the only unknown. Solving this equation, contact radius a an be calculated and, finally, contact force from [3].

Even contact force signal 54 is preferably an electric signal. Similarly to detection signal 51, it can be a continuous signal responsive to detected force F and ranging between predetermined voltage or current minimum and maximum values (conventionally 4-20 mA), corresponding to minimum and maximum force values, or vice-versa, of a predetermined pressure range.

Contact force signal 54 is delivered by processing unit 60 to a notification device 70 of the instrument, via a conventional electrical connection means such as a wire 33, in order to notify contact force F to a user. Notification device 70 can include, for example, an analogue or digital display 71, arranged at a portion of instrument 1 visible or accessible to the user, for instance, it can be also integrated to support member 11. This will more in detail described hereinafter as an example, with reference to FIG. 26.

With reference to FIGS. 4 to 6, in a possible modification of instrument 1, gas-inflatable balloon 20 comprises a rigid back portion 27 configured to lay on lateral portion 11' of support member 11 or on a flat surface provided inside recess 12 if provided, and also comprises an inflatable front portion 28 opposite to rigid back portion 27. Entrance portion 23 protrudes from rigid back portion 27 and is configured to engage with connection member 13 arranged on the flat surface lateral portion 11' of support member 11 or on the flat surface provided inside recess 12, if any.

FIG. 7 shows an instrument 2 according to another exemplary embodiment of the invention, which differs from instrument 1 essentially in that the detector is a strain gage 42 instead of pressure detector 41 (FIGS. 1-3).

Strain gage 42 is arranged to output a strain signal 52 responsive to a modification of a said stretch condition of a membrane 22 of gas-inflatable balloon 20. A strain or a stress of membrane 22 of gas-inflatable balloon 20 is therefore measured, instead of pressure P inside it, in order to determine contact force F. Strain signal 52 can be a continuous electric signal as indicated for pressure detection signal 51.

In particular, strain gage 42 can be embedded in membrane 22 or, as an alternative, it can lay on an external or internal surface of membrane 22 of gas-inflatable balloon 20.

Strain gage 42 is connected with processing unit 60 via a conventional electric connection means such as a wire 31 in order to deliver detection signal 52 to processing unit 60.

Processing unit 60 is configured to treat the strain or stress value of signal 52 as a force-related value, i.e. a value related to a contact force F that is exchanged between gas-inflatable balloon 20 and wall 90 (FIG. 3). In other words, contact force F is calculated as a function of excess pressure value $\Delta P$ by processing unit 60.

Even in this case, the relationship between F and the strain/stress value depends on some features of gas-inflatable balloon 20, and can be obtained by a calibration procedure similar to the one already described in connection with instrument 1 of FIGS. 1 to 3.

Other parts of instrument 2, such as support member 11, inflate/deflate assembly 30, 34, 35, notification device 70 and connections thereto, and the like, can be the same as in the embodiment of FIGS. 1 to 3, therefore they will not be described any further. It is useful to observe that a pressure sensor can be preferably provided also in this embodiment, so that processing unit 60, upon receiving the inflate input signals from a user, can control inflation/deflation valve assembly 34 to inflate gas-inflatable balloon 20 up to an inflate pressure so that the measurement can be performed.

FIGS. 8 and 10 show two instruments 3 and 4 according to respective modifications of a further exemplary embodiment of the invention. Instruments 3 and 4 differ from instrument 1 of FIGS. 1 to 3 and instrument 2 of FIG. 7 essentially in that the detector is an image detector 43,47 instead of pressure detector 41 (FIG. 1) or strain gage 42

(FIG. 7). Moreover, instruments 3 and 4 differ from instruments 1 and 2 in that gas-inflatable balloon 20 has a plurality of markers 24.

In instrument 3 (FIG. 8), image detector is arranged outside of gas-inflatable balloon 20, for example it can be an endoscopic video camera or endoscope 43. In particular, instrument 3 can be a minimally invasive surgical or diagnostic instrument and endoscope 43 can be provided to assist the operation of a diagnostic or surgical tool of instrument 3.

As an alternative (FIG. 10), image detector comprises an end portion of an optical fibre 47 arranged to detect a deformation of a surface portion of gas-inflatable balloon 20. This solution is preferred in the case of instrument 4, in which image detector 47 is arranged within gas-inflatable balloon 20, through entrance portion 23 of gas-inflatable balloon 20, but can be arranged outside of gas-inflatable balloon 20 all the same, like endoscope in FIG. 8.

Image detector 43 or 47 can be connected with processing unit 60 via a conventional connection means such as an optical fibre or a wire 31, as required by the image detector in use, in order to deliver detection signal 52 to processing unit 60.

In this case, the detection signal is therefore an image signal 53 of gas-inflatable balloon 20, in particular of a portion thereof, and of markers 24. During contact C of gas-inflated balloon 20 and a wall 90, image signal 53 is real time updated to show a modification of markers 24 due to contact C, for instance, a displacement and/or a shape change and/or a visually detectable number of markers 24.

In this exemplary embodiment of the invention, processing unit 60 is configured to identify this modification of markers 24 in image signal 53 by a and to calculate a deformation value of gas-inflatable balloon 20 due to contact C, as the value related to contact force F. In other words, processing unit 60 includes computer-imaging means configured to obtain deformation value of gas-inflatable balloon 20 from bi- or three-dimensional image of gas-inflatable balloon 20, which is included in image signal 53.

The deformation of gas-inflatable balloon 20 can be for example a flattening x as a consequence of contact C with wall 90 (FIG. 8,10), with respect to round shape, in particular a spherical shape, it had once inflated to initial inflate pressure $P_0$ and before contact C. As an alternative, the deformation can be a contact area A, as shown in FIG. 9, which is formed between gas-inflatable balloon 20 and wall 90 due to their mutual contact condition C.

Still in this embodiment, processing unit 60 is configured to treat deformation value, for instance, x or A, as the force-related value, in other words, contact force F is calculated as a function of deformation value, for instance, x or A.

The relationship between F and the deformation x or A of gas-inflatable balloon 20 depends on some features of the latter, firstly on material, thickness and initial inflate pressure $P_0$. In the case of flattening x as measured value, the function expressing contact force F can have the form:

$$F = K x, \quad [2]$$

where K is a compliance parameter of gas-inflatable balloon 20, depending on the material and on the membrane thickness, and on initial inflate pressure $P_0$.

In other words, even in this case, the relationship between F and deformation x or A depends on some features of gas-inflatable balloon 20, and can be obtained by a calibration procedure similar as described in connection with instrument 1 of FIGS. 1 to 3.

Other parts of instruments 3 and 4, such as support member 11, inflate/deflate assembly 30, 34, 35, notification device 70 and connections thereto, and the like, can be the same as in the embodiment of FIGS. 1 to 3, therefore they will not be described any further. It is useful to observe that a pressure sensor can be preferably provided also in this embodiment, so that processing unit 60, upon receiving the input signal from a user, can control inflation/deflation valve assembly 34 to inflate gas-inflatable balloon 20 up to an inflate pressure so that the measurement can be performed.

Figure 11:
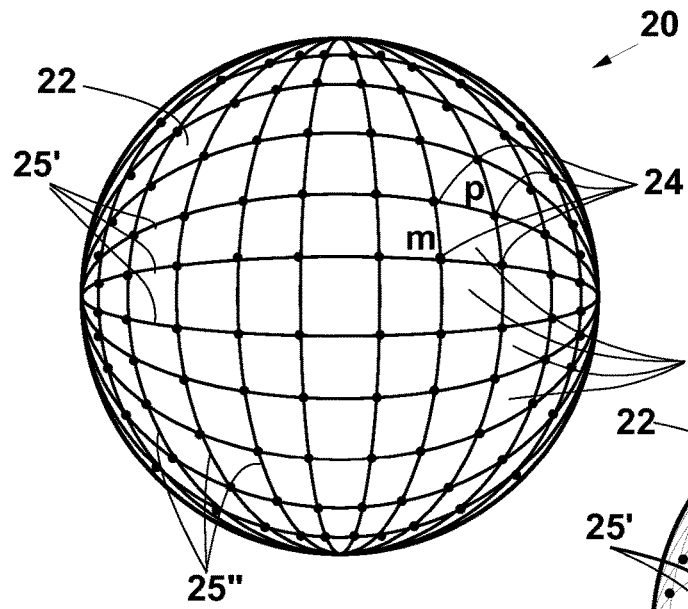
FIGS. 11-18 diagrammatically show gas-inflatable balloons suitable for the instrument of FIGS. 8 and 10, in the inflated state and in which markers are provided in different forms.
Figure 12:
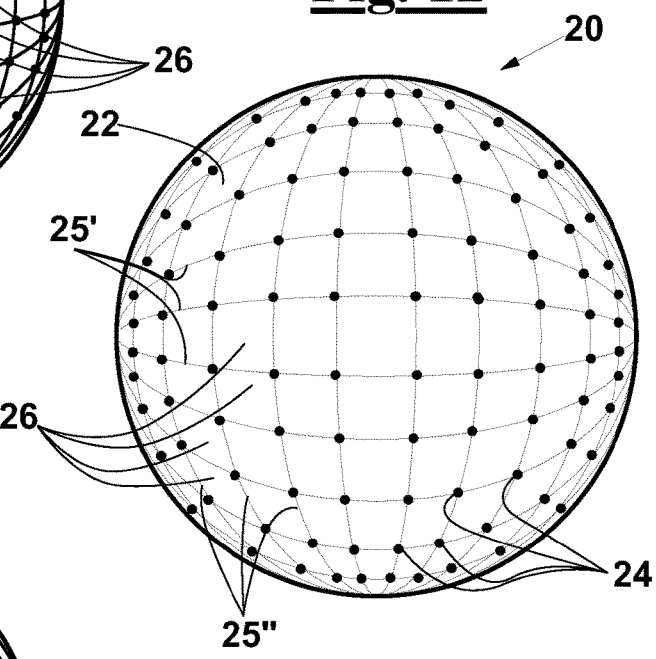
Figure 13:
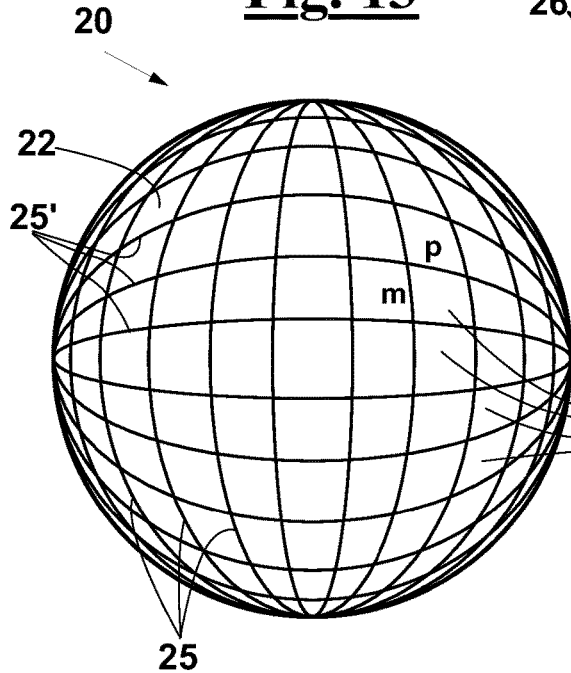

FIG. 11 shows a gas-inflatable balloon 20 according to a specific embodiment thereof and suitable for use with instrument 3 or 4 of FIGS. 8-10. Gas-inflatable balloon 20 has a plurality of markers, i.e. reference signs 24. In this case, markers are small reference areas or points 24 arranged according to a predetermined pattern. In particular, reference points 24 are arranged according to a regular mesh or matrix. For example, in the arrangement of FIG. 11 the distances m between adjacent reference points 24, measured along the meridians 25" on membrane 22 of gas-inflatable balloon 20 are equal to each other, as well as the distances p similarly measured along the parallels 24, in particular m=p.

Figure 14:
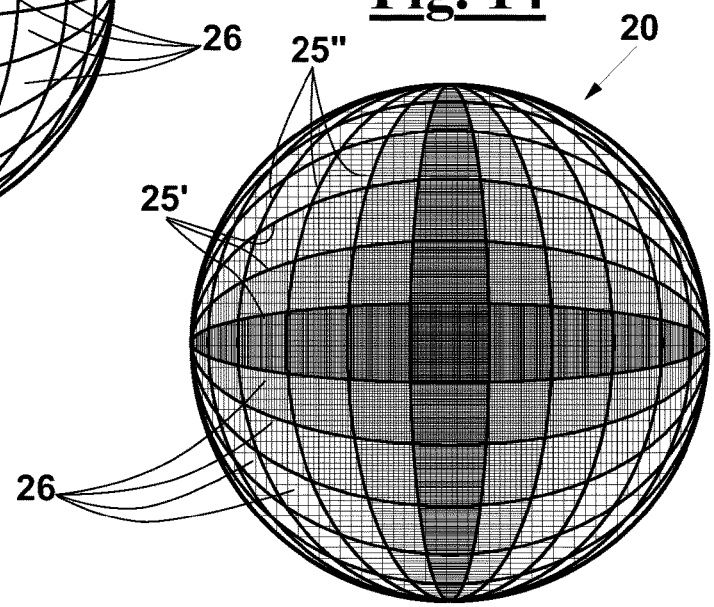
Figure 15:
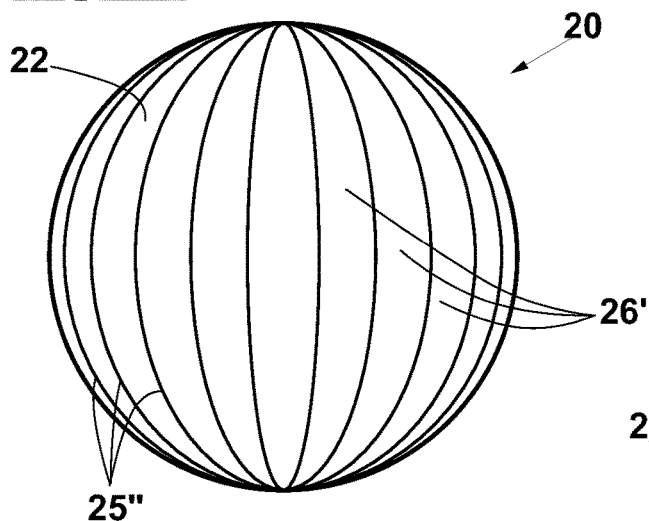
Figure 16:
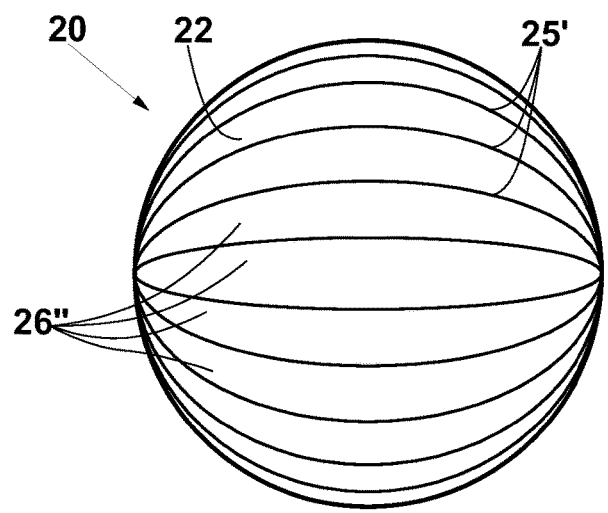
Figure 17:
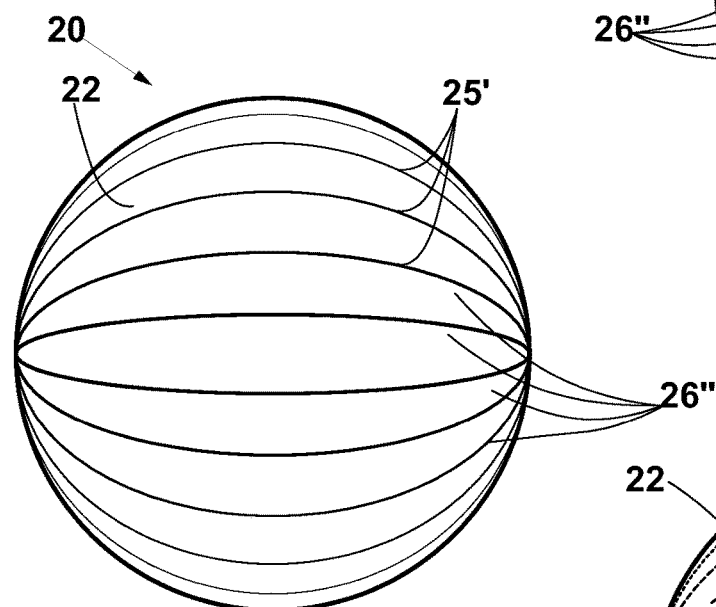
Figure 18:
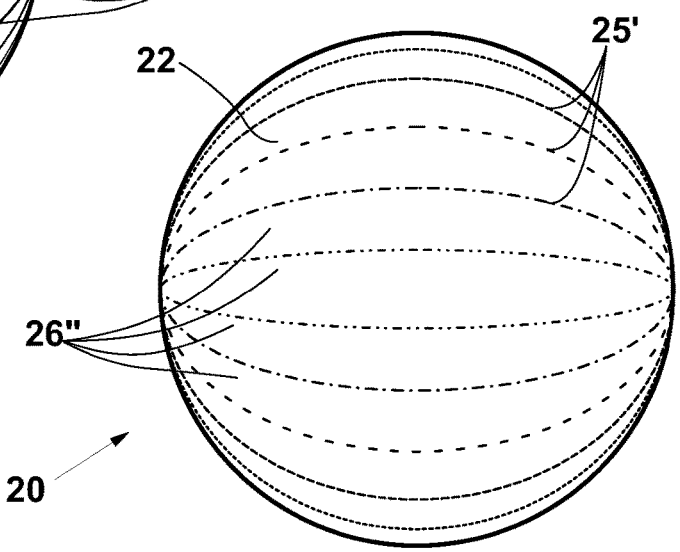

FIGS. 11 to 18 show gas-inflatable balloons 20 according to some embodiments, in connection with the form of the markers. In an embodiment, parallel and meridians 25',25" can be or just ideal connection lines (FIG. 12) connecting reference points 24 or real, visually detectable lines (FIG. 11,13) marked on membrane 22, in other words, parallels 25' and meridians 25" can be markers themselves. In particular, the markers can comprise meridians 25" and/or parallel only (FIGS. 15-18), the intersections between parallels 25' and meridians 25" having no additional visual impact on printed membrane 22. In a modification of the above embodiment, the tetragons defined by specific pairs of opposite sides m and p can have a corresponding colour and/or colour tonalities codifying the position of each tetragon on the surface of membrane 22 (FIG. 14). In still another embodiment, only parallel 25' are visually detectable on the surface of membrane 22 (FIGS. 16-18) by lines of different thickness (FIG. 17) and/or different colour (not shown) and/or different colour tonality (not shown) and/or grayscale (FIG. 17) and/or parallels 25' are marked by lines having different patterns (FIG. 18), i.e. dashed and/or dotted lines according to dot and/or dash sequences different from each other.

As explained with some examples, to use such a gas-inflatable balloon 20, image detector 43 or 47 has to be arranged so as to see gas-inflatable balloon 20 and markers 24 displacing and/or being deformed and/or changing in number in a visually detectable region of gas-inflatable balloon 20, from an initial position and/or shape and/or number thereof, achieved once gas-inflatable balloon 20 has been inflated to initial inflate pressure $P_0$, the position of markers 24 referred to support element 11.

The computer-imaging means of processing unit 60 used in association with a gas-inflatable balloon providing markers 24 as described above is configured to identify these modifications of markers 24 in image signal 53. In some embodiments, the computer-imaging means is configured to count the number of markers such as points 24 and/or parallels 25' and/or meridians 25", and/or tetragons or more in general polygons 26 that disappear or appears in the image upon bringing gas-inflatable balloon 20 into contact with wall 90 to a given extent. In other embodiments, computer-imaging means is configured to recognize thickness and/or colour and/or colour tonality and/or grayscale tone and/or line pattern of such lines as visually detectable parallels 25" on membrane 22. In other embodiments, computer-imaging means is configured to recognize number and/or colour and/or colour tonality and/or grayscale tone of such areas as tetragons 26 on membrane 22.

Moreover, processing unit 60 and is configured to compute a deformation parameter of gas-inflatable balloon 20 from the above change. For example, in the case of markers 24 regularly arranged as in FIG. 11, contact area A is proportional to the number of disappearing/appearing reference points 24.

Advantageously, processing unit 60 is configured to determine the orientation of contact surface A and, accordingly, the direction of contact force F.

With reference to FIGS. 19 and 20, an instrument 5 according to a further exemplary embodiment of the invention is described, in which first and second gas-inflatable balloons 20 and 20' are releasably mounted to respective recess 12,12' of support member 11, and are arranged to switch from respective deflated states D to respective inflated states J, in the respective inflated states J first and second gas-inflatable balloons 20' protruding out of respective recesses 12,12'. Inflation/deflation valve assembly 34 is arranged to selectively connect first and second gas-inflatable balloons 20, 20' with gas source 30 or with gas-discharge vent and to inflate first and second gas-inflatable balloons 20, 20' to respective inflate pressures $P_{01}, P_{02}$.

In instrument 5, the detector is an image detector 43, more in particular two image detectors 43,43' are provided configured to output image signals 53,53' related to first and second gas-inflatable balloons 20 and 20', respectively. In this case, both balloons 20 and 20' comprise respective pluralities of markers, as described in connection with instruments 3 and 4 of FIGS. 8-10.

In respective modifications of instrument 5, the detector can be a pressure detector or a strain gage, as shown in FIG. 1 and in FIG. 7.

For instance, each of these deformations can be balloon flattening $\Delta x$ or contact surface A as shown in FIGS. 8 to 10.

Processing unit 60 is configured to receive detection signals 53 and 53', in this case image signals 53 and 53', and to calculate respective first and second contact force signal 54 and 54' from a deformation parameter of gas-inflatable balloons 20,20', respectively, according to a predetermined function. So configured, instrument 5 can provide data at two different position of wall 90, where a contact C occurs with gas inflatable balloons 20 and 20', respectively. Extending in an obvious way to any number of gas-inflatable balloons, instrument 5 can provide a gradient of a given property of wall 90 along a line thereon, in the form of values of that property at given positions of this line 90. As in previously described instruments 1 to 4, notification device 70 of a contact force is configured to receive and to notify contact force signals 54, 54' to the user.

Other parts of instrument 5, such as support member 11 or inflate/deflate assembly 30, 34, 35 can be suitably modified for the case of a plurality of balloons 20,20' in a way obvious for a skilled person, so they will not be described any further.

Referring now to FIG. 20, in a modification of this exemplary embodiment, gas-inflatable balloons 20 and 20' have stiffness different from each other, and the inflation/deflation valve assembly 34 is arranged to inflate the first and second gas-inflatable balloons 20,20' up to respective initial pressures $P_{o1}, P_{o2}$ different from each other such that the first and second gas-inflatable balloons 20, 20' have respective initial radiuses $R_1, R_2$ equal to each other. Moreover, processing unit 60 is configured to calculate a compliance parameter $K_s$ of wall 90 according to the formula $$Ks = \frac{F1 - F2}{\frac{F_2}{\pi P_{o2} R_2} - \frac{F_1}{\pi P_{o1} R_1}} \quad [11]$$

where $F_1$ and $F_2$ are forces obtained from first and second contact force signals 54 and 54', respectively, $P_{o1}$ and $P_{o2}$ are the initial gas pressure values inside gas-inflatable balloons 20 and 20', respectively, and $R_1$ and $R_2$ are the initial radiuses of gas-inflatable balloon 20 and 20', respectively. Besides, processing unit 60 is configured to generate a compliance signal 55 according to the calculated compliance parameter, and contact force-value notification device 70 is configured to receive and notify also the compliance signal 55 to said user.

Formula [11] is obtained as follows. From FIG. 20, where
$\Delta x_1, \Delta x_2$ are the flattenings of gas-inflatable balloon 20, 20' due to the contact with wall 90, with respect to undeformed configurations 20a and 20'a of gas-inflatable balloon 20, 20';
$\Delta s_1, \Delta s_2$ are the deformations of wall 90 corresponding to the deformations of gas-inflatable balloon 20, 20', i.e. at respective contact points or contact areas.

It is readily understood that $$(\Delta s_1 - \Delta s_2) = (\Delta x_2 - \Delta x_1). \quad [12]$$

On the other hand, the following relationships are also valid:

$$F_1 = F_{s1} \quad [13']$$

$$F_2 = F_{s2}, \quad [13'']$$

in other words, force $F_1, F_2$ acting on gas-inflatable balloons 20, 20' is equal to respective force $F_{s1}, F_{s2}$ received by wall 90 in the respective contact zones. This can be written making reference to compliance $K_s$, identical for two gas-inflatable balloon 20, 20', and to deformation $\Delta s_1, \Delta s_2$:

$$F_{s1} = K_s \Delta s_1 \quad [14']$$

$$F_{s2} = K_s \Delta s_2 \quad [14'']$$

therefore $(F_1 - F_2) = (F_{s1} - F_{s2}) = K_s(\Delta s_1 - \Delta s_2)$, i.e.:

$$(F_1 - F_2) = K_s(\Delta s_1 - \Delta s_2) \quad [15].$$

By combining [15] and [11] compliance $K_s$ can be expressed:

$$K_s = (F_1 - F_1)/(\Delta x_2 - \Delta x_1) \quad [16]$$

On the other hand, it is known[1] that in a gas-inflatable balloon initially inflated to initial inflate pressure $P_0$ and to initial radius R:

$$F = \pi P_0 a^2, a^2 = R\Delta x \quad [17', 17'']$$

and therefore:

$$F_1 = \pi P_{o1} R_1 \Delta x_1, \quad [18']$$

$$F_2 = \pi P_{o2} R_2 \Delta x_2, \quad [18'']$$

where subscript respectively 1 and 2 are used to indicate initial pressures and radiuses of gas-inflatable balloons 20 and 20'. An expression of the difference between $\Delta x_2$ and $\Delta x_1$ can be obtained from relationships [18'] and [18'']

$$\Delta x_2 - \Delta x_1 = \frac{F_2}{\pi P_{o2} R_2} - \frac{F_1}{\pi P_{o1} R_1} \quad [19]$$

which, introduced into relationship [16], gives $$Ks = \frac{F1 - F2}{\dfrac{F_2}{\pi P_{o2} R_2} - \dfrac{F_1}{\pi P_{o1} R_1}} \qquad [11]$$

A similar analytical reasoning can be made whatever the contact force-related value is.

Figure 23:
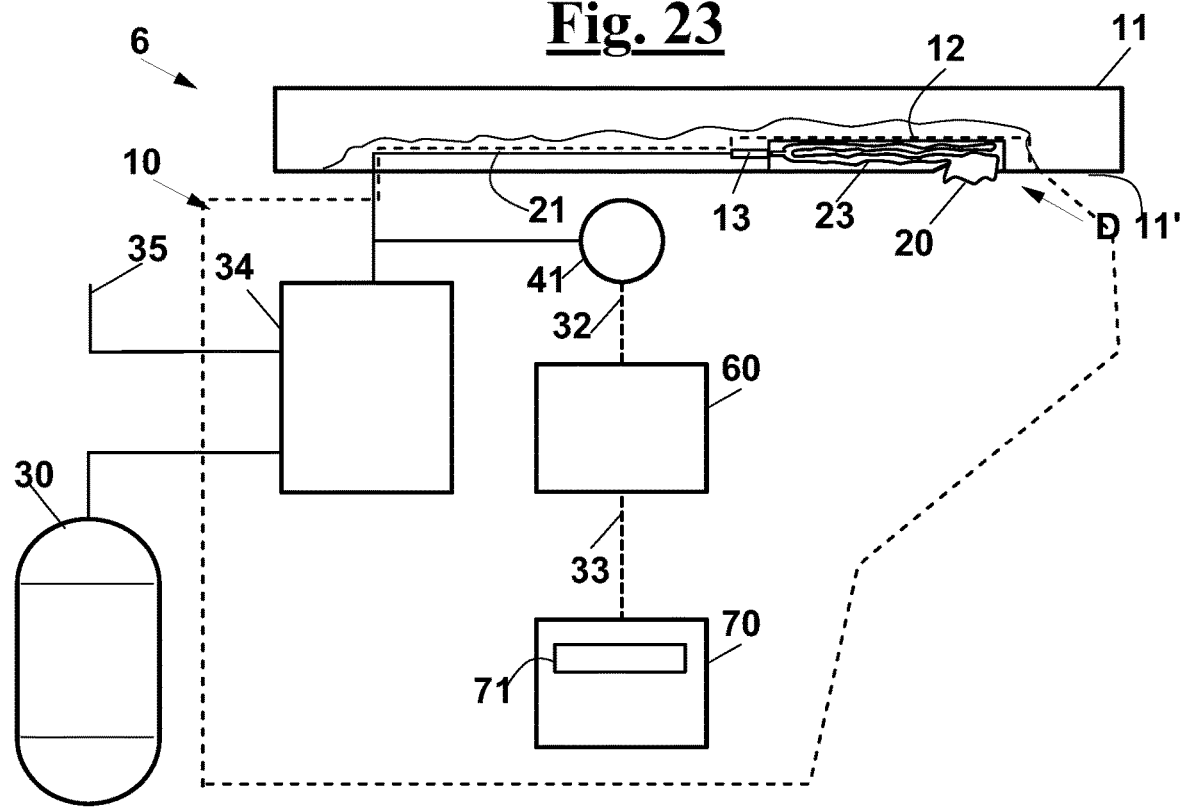
FIGS. 23 to 25 diagrammatically shows an instrument according to a further exemplary embodiment of the invention, in which the feed tube, the inflation/deflation valve assembly, the processing unit and the notification device are included in the contact sensor device integrated in the support member of the instrument, and in which the detector is a pressure detector, in the same conditions as FIGS. 1 to 3, respectively.
Figure 24:
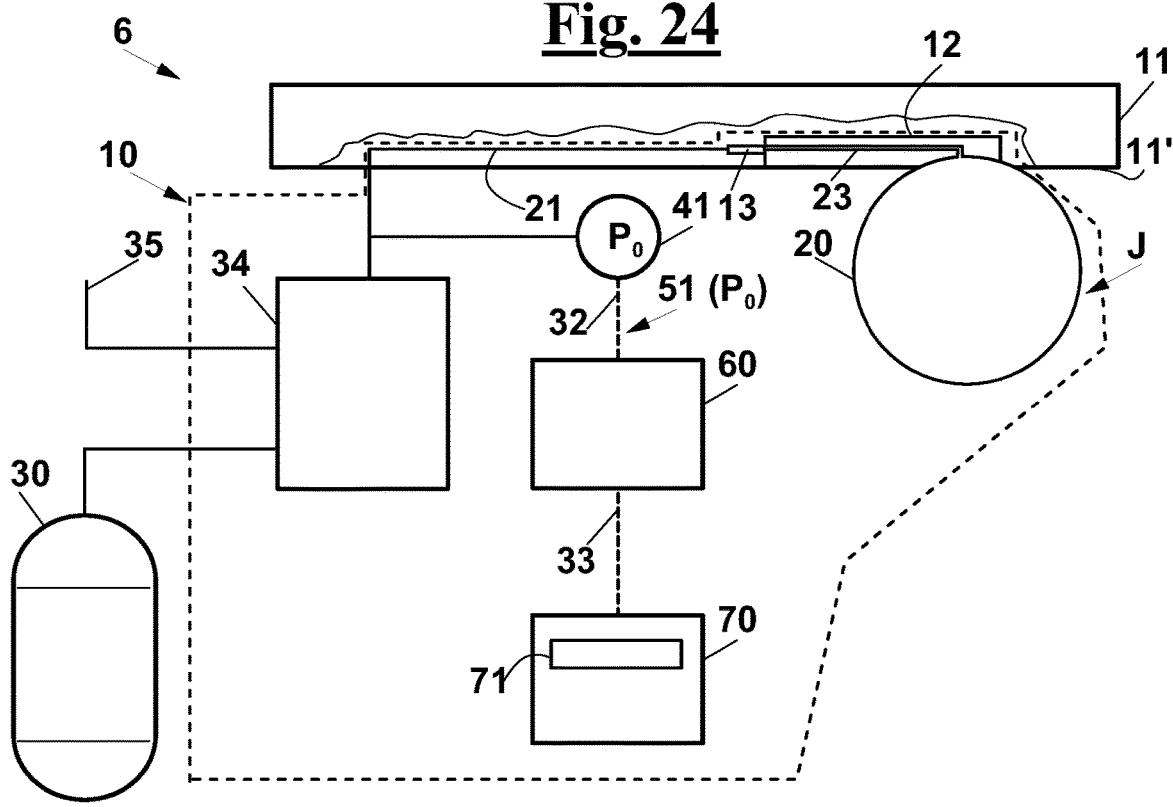
Figure 25:
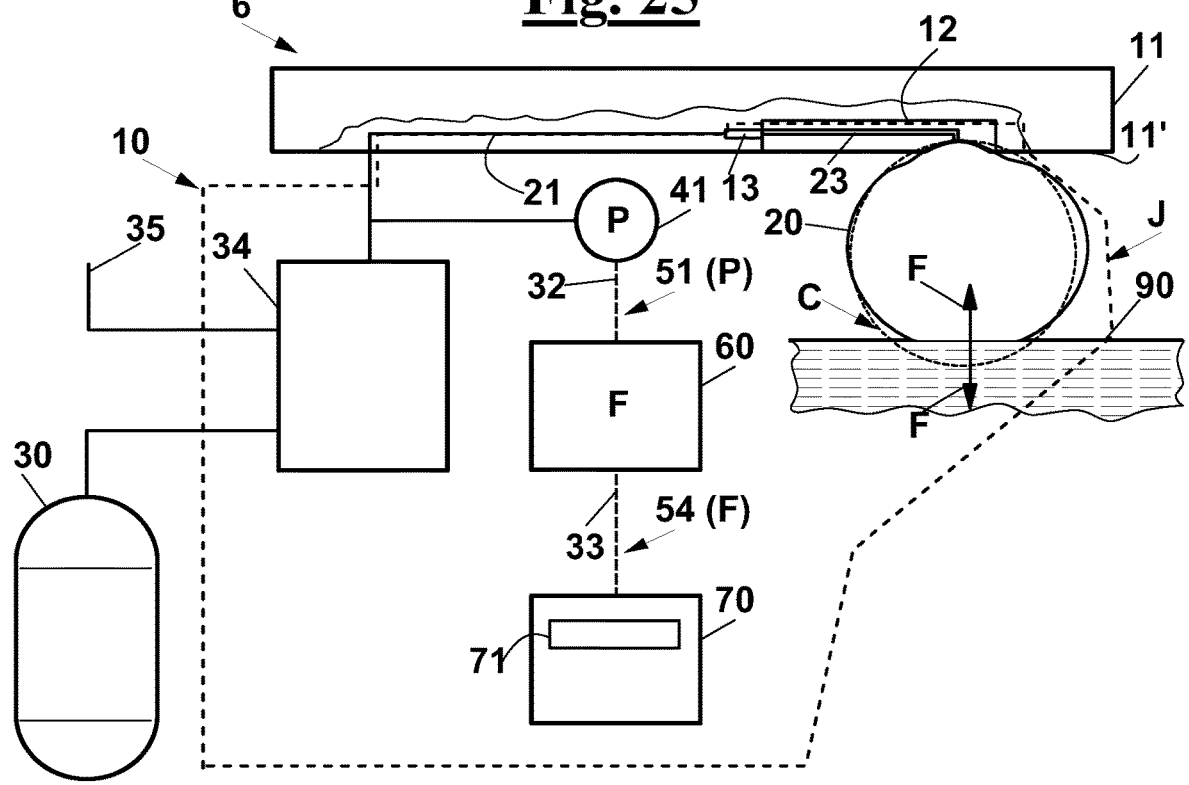

FIGS. 23 to 25 show an instrument 6 according to an exemplary embodiment of the invention, wherein contact force sensor device 10, includes feed duct 21, detector 41, processing unit 60, contact force-value notification device 70, which are therefore all integrated in support member 11. In other embodiments, not shown, at least one of feed duct 21, detector 41, processing unit 60, contact force-value notification device 70 can be included in sensor device 10 and therefore integrated in support member 11.

Figure 26:
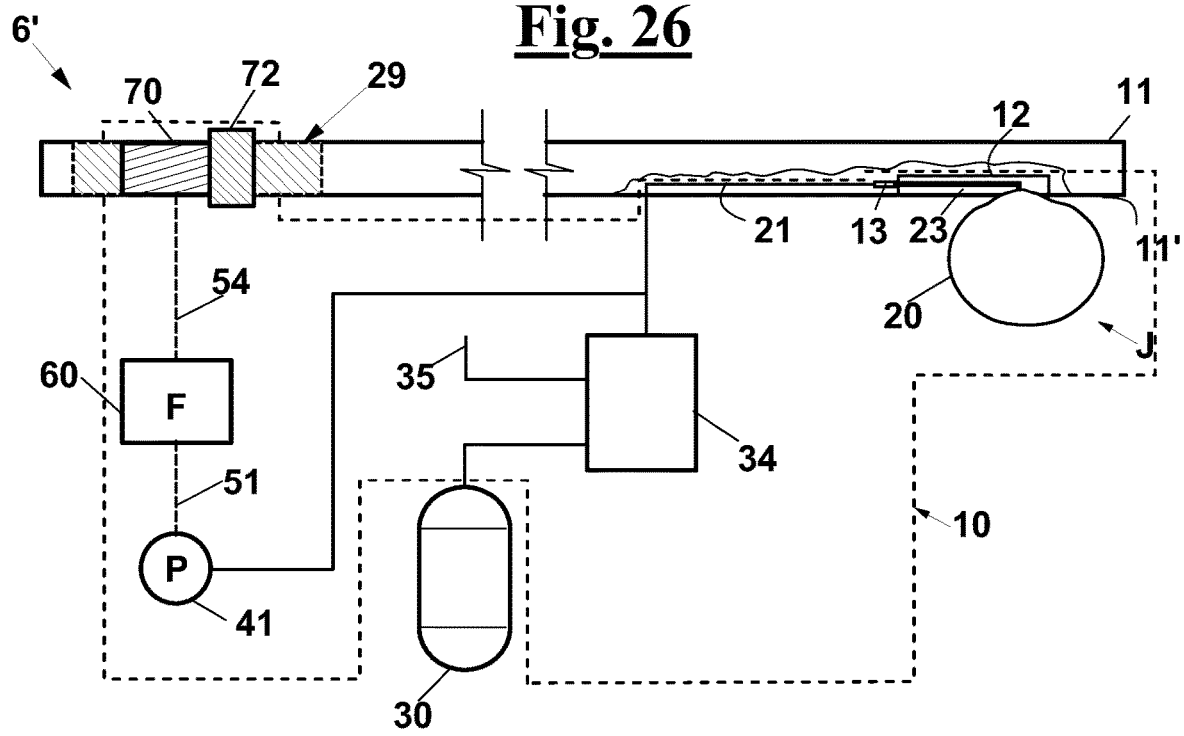
FIG. 26 diagrammatically shows an instrument according to a further exemplary embodiment of the invention, in which the contact force-value notification device is integrated in a handle portion of the instrument.

In particular, as shown in FIG. 26, in an advantageous exemplary embodiment, an instrument 6' comprises a handle 29, and notification device 70 is configured to provide contact force signal 54 to a user through an actuator 72 arranged at handle 29, in the form of a tactile feedback, in particular a vibrotactile feedback. For instance, instrument 6' can be a flexible diagnostic or surgical instrument, actuated by a surgeon from outside the patient's body, and suitable to travel along such extended lumina as vascular lumina or abdominal lumina. Even if only flexible instrument 6' is shown, in which the detector is a pressure detector 41, however, flexible instruments are obviously possible in which the detector is a strain gage or an image detector as in instruments 2 and 3 or 4, respectively.

As anticipated, the instrument according to the invention can have surgical or diagnostic application. In this case, wall 90 is a tissue or the wall of an organ in the patient's body, in particular, at an operation region or proximate thereto.

Figure 21:
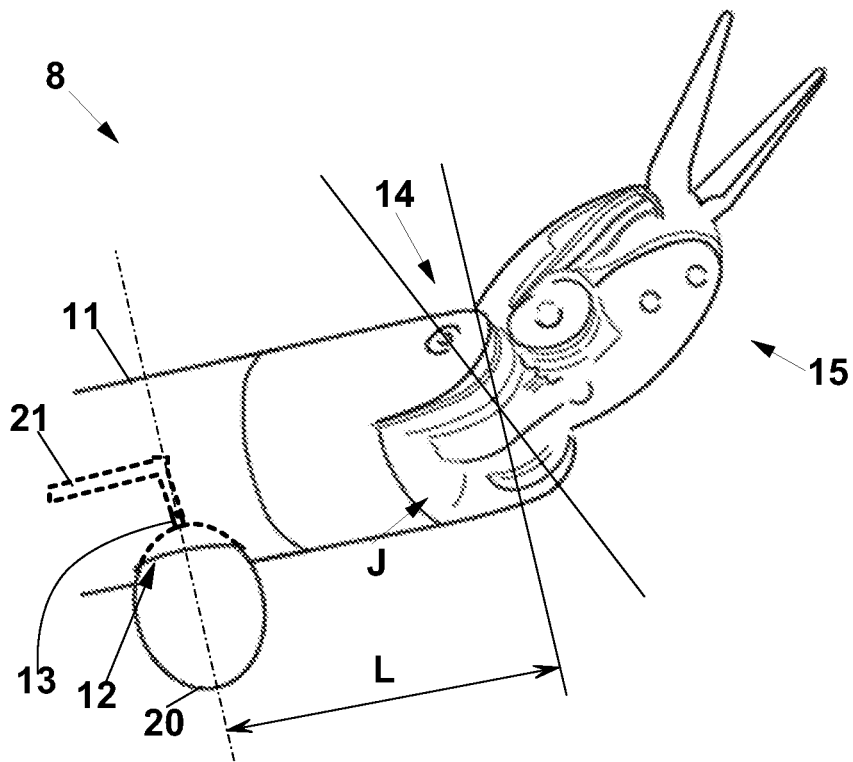
FIG. 21 diagrammatically shows an instrument according to a further exemplary embodiment of the invention, in which a surgical tool is provided at a distal end of the support member, at a predetermined distance from the gas-inflatable balloon, in an inflated state.
Figure 22:
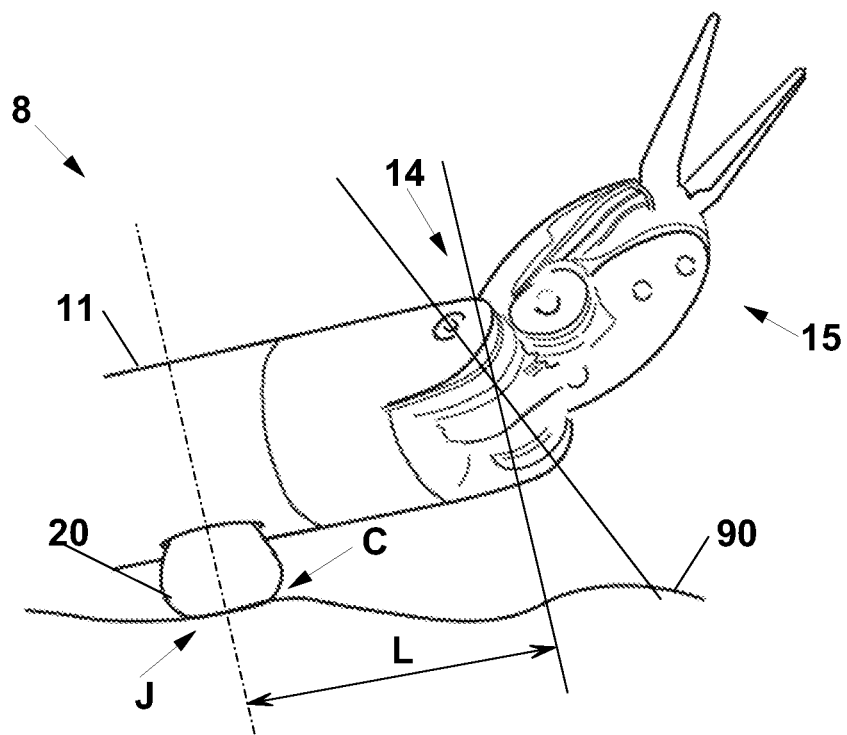
FIG. 22 shows the instrument of FIG. 21 in a measurement condition.

For instance, FIGS. 21 and 22 show an instrument 8 according to an exemplary embodiment of the invention, in which connection member 13 is arranged at a predetermined distance L from a distal end portion 14 of support member 11. Accordingly, also recess 12 and gas-inflatable balloon 20 are spaced apart from end portion 14, which avoids interference with a possible surgical or diagnostic tool 15 arranged at end portion 14. For example, instrument 8 of FIGS. 21 and 22 comprises a forceps 15 as a surgical tool. Gas-inflatable balloon 20 is shown in inflated state J, more in detail, FIG. 21 shows an initial condition of gas-inflatable balloon 20, while FIG. 22 show an condition in which a contact C is established between gas-inflatable balloon 20 and wall 90.

In some modifications of instrument 8, the tool arranged at distal end 14 of support portion 11 can be any surgical tool, or a diagnostic tool such as an endoscopic video camera.

In an exemplary embodiment of the invention, not shown, processing unit 60 of the instrument is configured to perform a sequence of measurements on wall 90 of a body tissue comprising steps of arranging gas-inflatable balloon 20 at a position of a plurality of predetermined positions on wall 90, inflating gas-inflatable balloon 20, computing force F or compliance $K_s$ at that position, possibly deflating gas-inflatable balloon 20, moving to another of those positions and repeating the measurement, and so on, so as to obtain an F- or $K_s$- map of wall 90.

Besides the surgical, diagnostic or therapeutic applications, other advantageous uses of the instrument of the invention are possible in such fields as remote or segregated manipulations of objects for research or manufacturing purposes. In this case, wall 90 can be the wall of an object to be manipulated in an environment far from an operator or segregated from him/her for safety reasons, such as a chemically and/or biologically and/or radioactively contaminated environment, and/or an environment at a temperature otherwise impossible to operate at.

Figure 27:
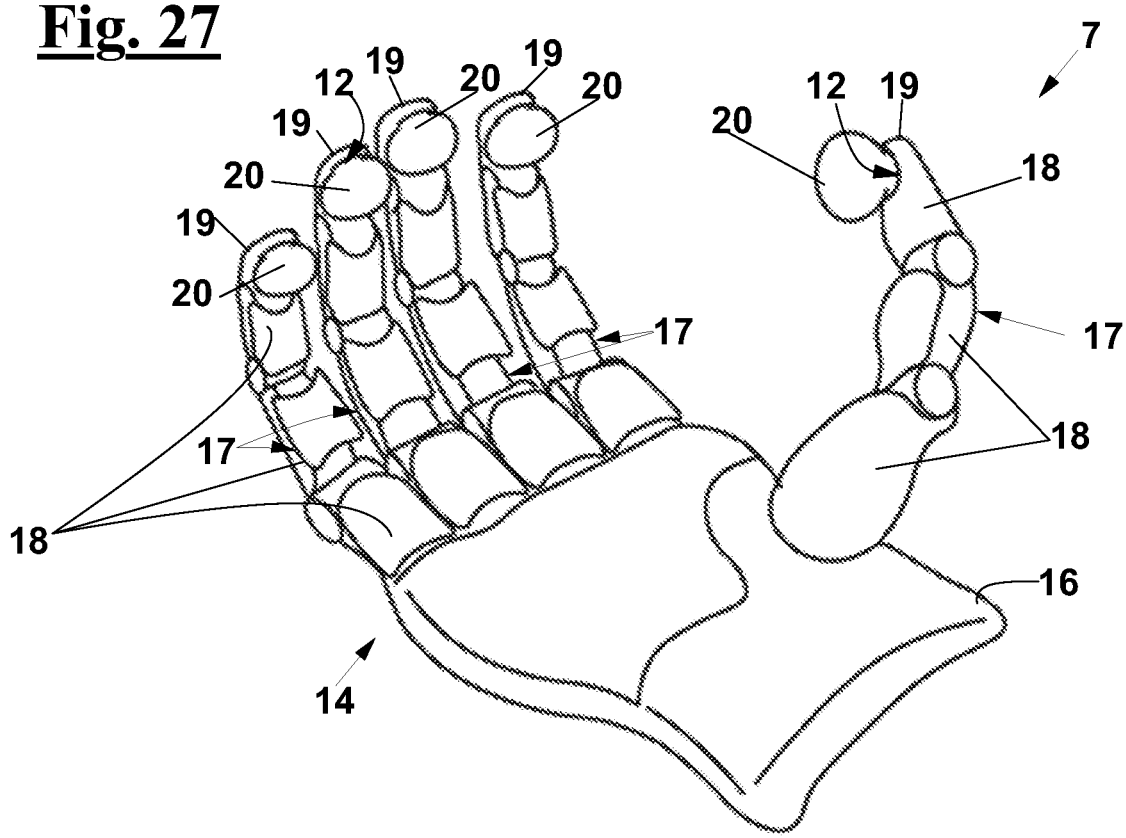
FIG. 27 diagrammatically shows a robotic hand including a plurality of instruments according to a further exemplary embodiment of the invention, these instruments having the shape of robotic fingers in which gas-inflatable balloons are arranged at the fingertips.
Figure 28:
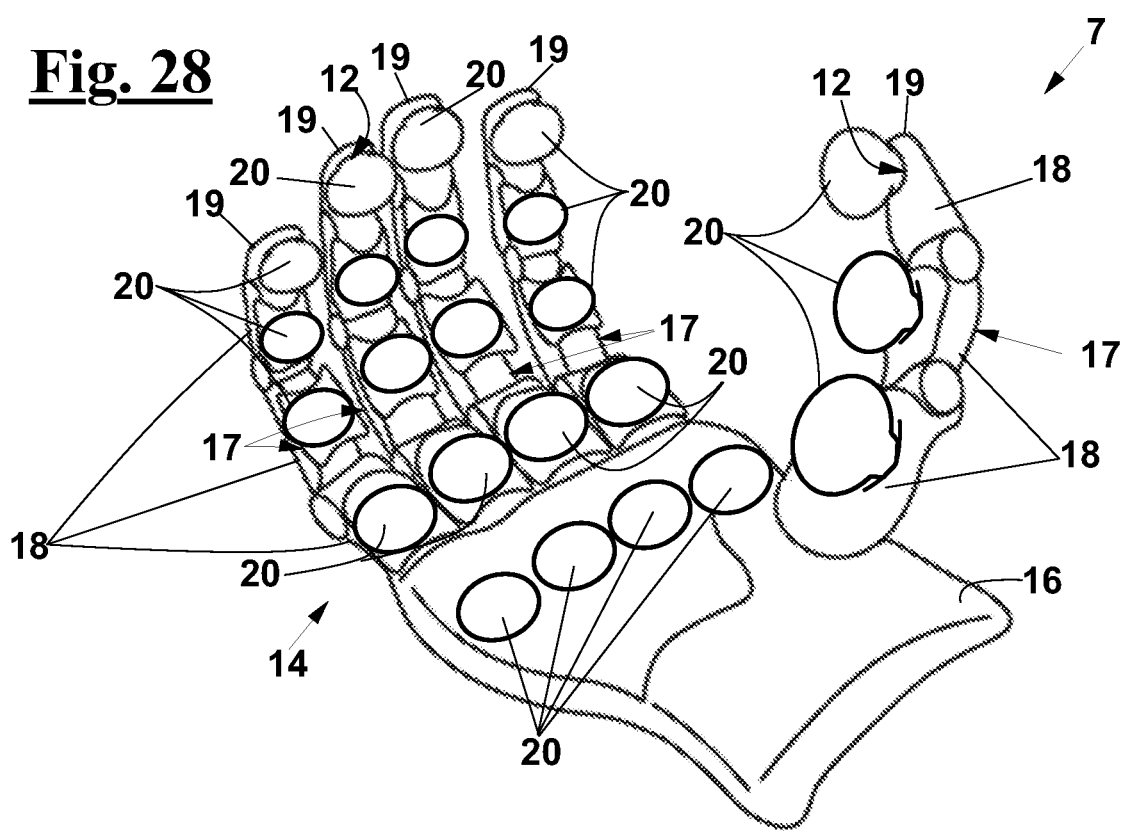
FIG. 28 diagrammatically shows a robotic hand similar to FIG. 27, in which the gas-inflatable balloons are also arranged on contact portions of the medial and proximal phalanx portions and on the palm of the robotic hand.

In this connection, FIGS. 27 and 28 show manipulators that are robotic hands 7,7', including a plurality of robotic fingers 17 extending from a palm portion 16, at least one of which 17' is opposable to the other robotic fingers 17. Each robotic finger 17 is an instrument according to the invention, comprising a plurality of sequentially arranged phalanx members 18 are mutually articulated in such a way to form a robotic finger (17) each finger 17 comprises a sensor device as described hereinafter, including a gas-inflatable balloon 20 mounted to a respective phalanx portion 18. The fingers 17 can have one or more sensor devices, including respective gas-inflatable balloon members. In particular, robotic hand 7 of FIG. 27 has one gas-inflatable balloon 20 provided only at a fingertip portion 19, while robotic hand 7 of FIG. 28 has a gas-inflatable balloon 20 provided on each phalanx member 18 and, optionally, one or more gas-inflatable balloons 20 at palm portion 16. Of course, in a modification not shown of instrument 7', only one part of phalanx members 18 can have gas-inflatable balloons 20. As anticipated, gas-inflatable balloons 20 can have respective entrance portions 23 engaged with respective connection member 13 arranged within a respective recess of phalanx member 18 so that to protrude out of phalanx member 18 only when in inflated state J, and to be contained within phalanx member 18 in inflated state J.

Figure 29:
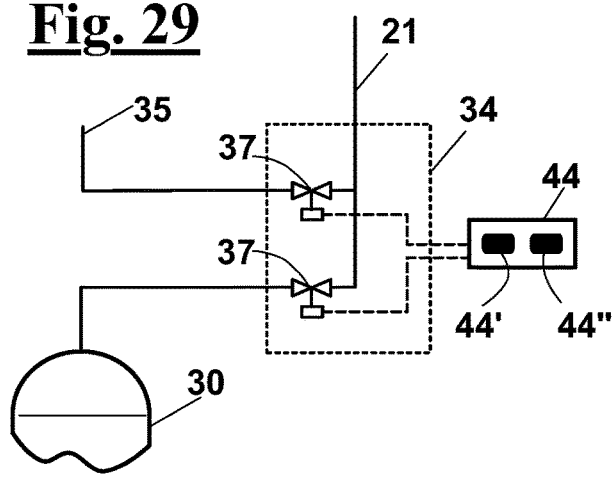
FIGS. 29 and 30 diagrammatically show the inflation/deflation valve assembly in two exemplary embodiments thereof.
Figure 31:
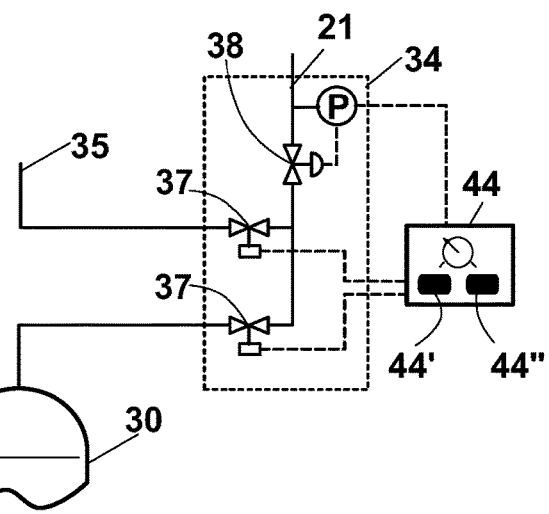
FIG. 31 shows the inflation/deflation valve assembly in an exemplary embodiment of the invention, in which a control valve is also provided, in order to adjust the gas inflation pressure of the gas-inflatable balloon at a predetermined value.
Figure 30:
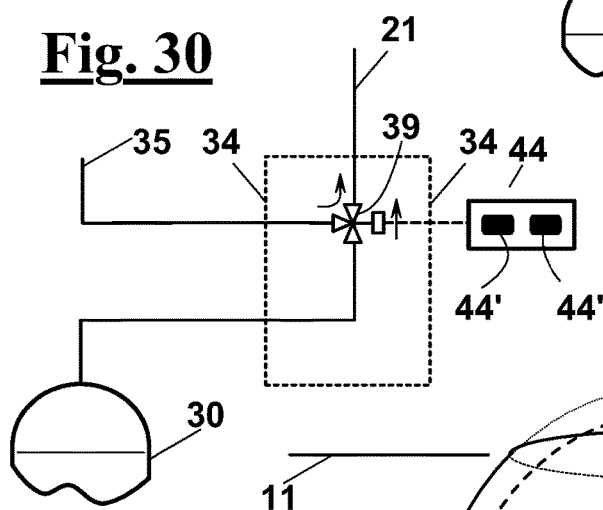

FIGS. 29 to 31 show three exemplary embodiments of inflation/deflation valve assembly 34 for selectively connecting gas-inflatable balloon 20 with gas source 30 or with gas-discharge vent 35. In FIG. 29, valve assembly 34 comprises two shut-off valves 37 mounted to connection ducts arranged between inflation/deflation duct 21, on one side, and gas source 30 or gas-discharge vent 35, on the other side. Valve assembly 34 also includes a control panel 44 comprising control buttons 44', 44" arranged to open/close shut-off valves 37. Valve assembly 34 of FIG. 30 differs from that of FIG. 29 only in that a three-way valve 39 is provided instead of a pair of two-way valves 37. The three ports of three-way valve 39 are pneumatically connected with gas-inflatable balloon 20, gas source 30 and with gas-discharge vent 35, respectively, and control panel 44 is configured to connect gas-inflatable balloon 20 in connection with either gas source 30 or gas-discharge vent 35.

In FIG. 31, inflation/deflation valve assembly 34 also comprises a pressure control valve 38 preferably mounted to a connection duct between inflation/deflation duct 21 and configured to adjust the pressure of the gas provided to gas-inflatable balloon 20 within a predetermined range of values or according to predetermined pressure values.

The foregoing description exemplary embodiments and examples of the invention will so fully reveal the invention according to the conceptual point of view, so that others, by applying current knowledge, will be able to modify and/or adapt for various applications such embodiments without further research and without parting from the invention, and, accordingly, it is to be understood that such adaptations and modifications will have to be considered as equivalent to the specific embodiments. The means and the materials to put into practice the different functions described herein could have a different nature without, for this reason, departing from the field of the invention. It is to be understood that the phraseology or terminology that is employed herein is for the purpose of description and not of limitation.

REFERENCES

1. F. Barbagli et al., "Simulating human fingers; a Soft finger Proxy Model and Algorithm", Proceedings of the 12$^{th}$ International Symposium on Haptic Interfaces for Virtual Environment and Teleoperation Systems (HAPTICS 04), 2004

The invention claimed is:

1. An instrument (1,2,3,4,5,6,6',7,8) comprising a support member (11) having a lateral surface (11'), and a contact force sensor device (10) that is integrated in said support member (11), said contact force sensor device (10) including:
   a gas-inflatable balloon (20) arranged to switch between a deflated state (D), and an inflated state (J) at an inflation pressure ($P_0$) and arranged to protrude from said lateral surface (11') of said support member (11) when in said inflated state (J),
said instrument comprising:
   a feed duct (21) arranged to feed a gas to said gas-inflatable balloon (20) through a connection member (13) engaged by an entrance portion (23) of said gas-inflatable balloon (20);
   an inflation/deflation valve assembly (34) arranged to selectively connect said gas-inflatable balloon (20) with a gas source (30) or with a gas-discharge vent (35), respectively, through said feed duct (21);
   a detector (41,42,43) configured to output a detection signal (51,52,53) responsive to a contact force-related value related to a contact force (F) acting on said gas-inflatable balloon (20) when said gas-inflatable balloon (20) is in said inflated state (J) and is engaged in a contact (C) with a wall (90) of a body outside of said support member (11);
   a processing unit (60) configured to:
      receive an inflate input signal from a user;
      upon receiving said inflate input signal, cause said inflation/deflation valve assembly (34) to inflate said balloon to said inflated state (J);
      receive said detection signal (51,52,53) and compute a contact force signal (54) responsive to said detection signal (51,52,53) according to a predetermined function;
      wherein said function is a relationship between said contact force and said force-related value selected from the group comprised of:
         said contact pressure (P);
         a deformation value (x,A) of said gas-inflatable balloon (20);
         a modification of a stretch condition of said membrane (22),
      said force-related value generated when said gas-inflatable balloon (20) is in contact with said wall (90),
      receive a deflate input signal from said user;
      upon receiving said deflate input signal, deflate said gas-inflatable balloon (20) to said deflated state (D),
   a contact force-value notification device (70) configured to receive said contact force signal (54) from said processing unit (60) and to notify to a user said contact force signal (54) responsive to said contact force (F).

2. The instrument (1,2,3,4,5,6,6',7,8) according to claim 1, wherein said support member (11) comprises a recess (12), and said connection member (13) is arranged within said recess (12), said gas-inflatable balloon (20) and said recess (12) arranged in such a way that said gas-inflatable balloon (20)
   is contained within said recess (12) when in said deflated state (D), and
   protrudes from said recess (12) when in said inflated state (J).

3. The instrument according to claim 1, wherein said gas-inflatable balloon (20) comprises a rigid back portion (27) configured to lay on said lateral surface (11') of said support member (11), and an inflatable front portion (28) opposite to said rigid back portion (27), wherein said entrance portion (23) protrudes from said rigid back portion (27) and has an engagement means to engage with said connection member (13).

4. The instrument (3,4) according to claim 1, wherein
   said gas-inflatable balloon (20) has a plurality of markers (24,25',25",26);
   said detector is an image detector (43) arranged to
      detect an image of said gas-inflatable balloon (20) and of said markers (24,25',25",26), so as to detect a modification of said markers (24,25',25",26) due to said contact (C) of said gas-inflatable balloon (20) in said inflated state (J) and a wall (90);
      output an image signal (53) as said detection signal;
   said processing unit (60) comprises:
      an image-processing means configured to identify said modification of said markers (24,25',25",26) in said image signal (53) and to calculate said force-related deformation value (x,A) of said gas-inflatable balloon (20) due to said contact (C), as said force-related value related to said contact force (F);
      a force-computing means configured to compute said contact force signal (54) comprising force values (F) responsive to said force-related deformation value (x,A) according to said predetermined function.

5. The instrument (3,4) according to claim 4, wherein said plurality of markers comprises a plurality of reference points (24), and said image-processing means is configured to:
   count a number of said reference points (24) that disappear, due to said contact (C), from a portion of said image in said image signal (53);
   calculate said force-related deformation value (x,A) from said number of disappeared reference points (24).

6. The instrument (3,4) according to claim 4, wherein said force-related deformation value of said gas-inflatable balloon (20) is selected between:
   a flattening length (x) due to said contact (C);
   a contact surface area (A) created by said contact (C).

7. The instrument (3,4) according to claim 4, wherein said image detector is arranged at a position selected between:
   a position outside said gas-inflatable balloon (20), and
   a position inside said gas-inflatable balloon (20), in particular, proximate to said entrance portion (23).

8. The instrument (1,6,6') according to claim 1, wherein:
   said detector is a pressure detector (41) arranged to
      detect said contact pressure (P), as said contact force-related value, between said inflation/deflation valve assembly (34) and said gas-inflatable balloon (20) when said gas-inflatable balloon (20) is contact with said wall (90);
      output a pressure signal (51) as said detection signal;
   said processing unit (60) is configured to:
      compute said contact force signal (54) comprising force values (F) responsive to said contact pressure value (P) according to said predetermined function.

9. The instrument according to claim 8, wherein said processing unit (60) is configured to calculate an excess pressure value (ΔP) equal to the difference between said contact pressure (P) and said inflation pressure ($P_0$) of said gas-inflatable balloon (20), and said function has the form:

$$F = a \cdot \Delta P - b \cdot \Delta P^2$$

wherein a and b are parameters depending on a material and on a thickness of a membrane (22) of said gas-inflatable balloon (20), and, for a given gas-inflatable balloon (20), on said inflation pressure ($P_0$).

10. The instrument according to claim 8, wherein said processing unit (60) is configured to:
   calculate a plurality of values of an energy amount received by said instrument upon said contact (C) between said gas-inflatable balloon (20) and said wall (90) at different values of a couple of deformation parameters (x,R) of said gas-inflatable balloon (20), said energy comprising an energy portion associated to a deformation of said gas-inflatable balloon (20) and an energy portion associated to a compression of said gas within said gas-inflatable balloon (20), due to said contact (C);
   calculate a relationship between said deformation parameters (x,R) based on an equation of state of said gas, so as to obtain said values of said energy amount as a relationship with only one deformation parameter (x,A) of said deformation parameters;
   calculate said contact force (F) as a product between said contact pressure (P) as a relative pressure and contact surface area (A) of said gas-inflatable balloon (20) and said wall.

11. The instrument (2) according to claim 1, wherein said detector is a strain gage (42) integrally arranged along a surface of a membrane (22) of said gas-inflatable balloon (20), said strain-gage (42) configured to:
   detect said modification of a stretch condition of said membrane (22) due to a contact (C) of said gas-inflatable balloon (20) in said inflated state (J) and a wall (90);
   output a strain signal (52) responsive to said modification of said stretch condition, as said detection signal;
   said processing unit (60) is configured to compute said contact force signal (54) comprising force values (F) responsive to said strain signal (52) according to said predetermined function.

12. The instrument (2) according to claim 11, wherein said strain gage (42) is arranged at a position selected between:
   a position embedded in said membrane (22) of said gas-inflatable balloon (20);
   a position on a surface of said membrane (22) of said gas-inflatable balloon (20).

13. The instrument (5) according to claim 1, wherein said gas-inflatable balloon is a first gas-inflatable balloon (20) and said detection signal is a first detection signal (53), and said contact force sensor device (10) also comprises:
   at least one second gas-inflatable balloon (20') arranged to switch between a deflated state (D), and an inflated state (J), wherein said second gas-inflatable balloon (20') is arranged to protrude from said support member (11) when in said inflated state (J),
   a second feed duct (21') arranged to feed a gas to said second gas-inflatable balloon (20') through a second connection member (13) engaged by a second entrance portion (23') of said second gas-inflatable balloon (20');

wherein:
   said inflation/deflation valve assembly (34) is arranged to selectively connect said second gas-inflatable balloon (20') with said gas source (30) and with said gas-discharge vent (35) through said second feed duct (21');
   said detector device (43,43') is configured to output also a second detection signal (53') according to a force-related value related to a second contact force ($F_2$) acting on said second gas-inflatable balloon (20');
   said processing unit (60) is configured to:
      receive said second detection signal (53');
      compute a second contact force signal (54') according to said predetermined function.

14. The instrument (5) according to claim 13, wherein:
   said inflation/deflation valve assembly (34) is arranged to inflate said first and second gas-inflatable balloons (20, 20') up to respective initial pressures ($P_{01}, P_{02}$) different from each other such that said first and second gas-inflatable balloons (20, 20') have respective initial radiuses ($R_1, R_2$) equal to each other;
   said processing unit (60) is configured to compute a compliance parameter ($K_s$) of said wall (90) according to the formula:

$$Ks = \frac{F1 - F2}{\dfrac{F_2}{\pi P_{o2} R_2} - \dfrac{F_1}{\pi P_{o1} R_1}}$$

where
      $F_1$ and $F_2$ are forces obtained from said first and second contact force signals (54,54'), respectively;
      $P_{o1}$ and $P_{o2}$ are said initial gas pressure within said first and second gas-inflatable balloons (20,20'), respectively;
      generate also a compliance signal (55) responsive to said calculated compliance parameter ($K_s$);
   wherein said contact force-value notification device (70) is configured to receive and to notify also said compliance signal (55) to said user.

15. The instrument (6) according to claim 1, wherein said contact force sensor device (10) includes at least one of:
   said feed duct (21);
   said detector (41);
   said processing unit (60);
   said contact force-value notification device (70);
   a combination thereof,
integrated in said support member (11).

16. The instrument (6') according to claim 1, comprising a handle portion (29) and said contact force-value notification device (70) comprises an actuator (72), in particular a vibrotactile actuator, arranged at said handle portion (29), so as to provide said contact force signal (54) to said user in the form of a tactile feedback.

17. The instrument (8) according to claim 1, wherein a surgical or diagnostic tool is arranged at a distal end portion (14) of said support member (11), and said connection member (13), engaged by said gas-inflatable balloon (20) through said entrance portion (23), is arranged at a predetermined distance (L) from said distal end portion (14).

18. The instrument according to claim 1, wherein said support member (11) comprises a plurality of sequentially arranged phalanx support members (14,18) that are mutually articulated in such a way to form a robotic finger (17);

said gas-inflatable balloon (20) is arranged on at least one of said phalanx support members (18);

said processing unit (60) is configured to provide said contact force signal (54) to a drive unit of said robotic finger (17) such that said drive unit can adjust a grip force of said robotic finger (17) responsive to said contact force (F).

19. A robotic hand (7) including a plurality of robotic fingers (17) comprising the instrument according to claim 18.

20. The instrument according to claim 1, wherein said inflation/deflation valve assembly (34) comprises a pressure-adjustment valve (38) configured to adjust a pressure ($P_O$) of said gas provided to said gas-inflatable balloon (20) in said inflated state (J) within a predetermined range of pressures values or according to predetermined pressure values, in particular, said range of pressure values is set between 4 and 12 kPa.

* * * * *